(12) United States Patent
Brinkmann et al.

(10) Patent No.: US 11,673,968 B2
(45) Date of Patent: Jun. 13, 2023

(54) ANTI-BRDU ANTIBODIES AND METHODS OF USE

(71) Applicant: Hoffmann-La Roche Inc., Little Falls, NJ (US)

(72) Inventors: Ulrich Brinkmann, Weilheim (DE); Guy Georges, Habach (DE); Johannes Auer, Schwaigen (DE); Wilma Lau, Munich (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/293,478

(22) Filed: Mar. 5, 2019

(65) Prior Publication Data
US 2020/0002437 A1    Jan. 2, 2020

Related U.S. Application Data

(63) Continuation of application No. 15/382,329, filed on Dec. 16, 2016, now abandoned, which is a continuation of application No. PCT/EP2015/064322, filed on Jun. 25, 2015.

(30) Foreign Application Priority Data

Jun. 26, 2014    (EP) .................................... 14174043

(51) Int. Cl.
| | | |
|---|---|---|
| *C07K 16/00* | (2006.01) | |
| *C07K 16/44* | (2006.01) | |
| *C07K 16/28* | (2006.01) | |
| *A61K 47/62* | (2017.01) | |

(Continued)

(52) U.S. Cl.
CPC ............ *C07K 16/44* (2013.01); *A61K 47/549* (2017.08); *A61K 47/62* (2017.08); *A61K 47/6803* (2017.08); *A61K 47/6879* (2017.08); *C07K 16/2881* (2013.01); *C07K 2317/24* (2013.01); *C07K 2317/31* (2013.01); *C07K 2317/55* (2013.01); *C07K 2317/622* (2013.01); *C07K 2317/624* (2013.01)

(58) Field of Classification Search
CPC ............... C07K 16/44; C07K 16/2881; C07K 2317/24; C07K 2317/31; C07K 2317/55; C07K 2317/622
See application file for complete search history.

(56) References Cited

U.S. PATENT DOCUMENTS

| | | |
|---|---|---|
| 4,676,980 A | 6/1987 | Segal et al. |
| 4,737,456 A | 4/1988 | Weng |
| 4,808,614 A | 2/1989 | Hertel |

(Continued)

FOREIGN PATENT DOCUMENTS

| | | |
|---|---|---|
| BR | 112014029403 A2 | 10/2018 |
| EA | 201000091 A1 | 6/2010 |

(Continued)

OTHER PUBLICATIONS

Rabia et al., Biochem Eng J. Sep. 15, 2018; 137: 365-374 (Year: 2018).*

(Continued)

*Primary Examiner* — Lei Yao
(74) *Attorney, Agent, or Firm* — Morrison & Foerster LLP

(57) ABSTRACT

The invention provides anti-BRDU antibodies and methods of using the same.

3 Claims, 1 Drawing Sheet
Specification includes a Sequence Listing.

(51) Int. Cl.
*A61K 47/68* (2017.01)
*A61K 47/54* (2017.01)

(56) References Cited

U.S. PATENT DOCUMENTS

| | | | |
|---|---|---|---|
| 4,816,567 A | 3/1989 | Cabilly | |
| 5,208,020 A | 5/1993 | Chari | |
| 5,416,064 A | 5/1995 | Chari | |
| 5,464,826 A | 11/1995 | Grindey | |
| 5,500,362 A | 3/1996 | Robinson | |
| 5,571,894 A | 11/1996 | Wels | |
| 5,587,458 A | 12/1996 | King | |
| 5,620,686 A | 4/1997 | Mason | |
| 5,624,821 A | 4/1997 | Wnter | |
| 5,635,483 A | 6/1997 | Pettit | |
| 5,648,237 A | 7/1997 | Carter | |
| 5,648,260 A | 7/1997 | Winter | |
| 5,712,374 A | 1/1998 | Kuntsmann | |
| 5,714,586 A | 2/1998 | Kunstmann | |
| 5,731,168 A | 3/1998 | Carter | |
| 5,739,116 A | 4/1998 | Hamann | |
| 5,767,285 A | 6/1998 | Hamann | |
| 5,770,701 A | 6/1998 | Megahren | |
| 5,770,710 A | 6/1998 | Megahren | |
| 5,773,001 A | 6/1998 | Hamann | |
| 5,780,588 A | 7/1998 | Pettit | |
| 5,789,199 A | 8/1998 | Pettit et al. | |
| 5,821,337 A | 10/1998 | Carter | |
| 5,840,523 A | 11/1998 | Simmons et al. | |
| 5,869,046 A | 2/1999 | Presta et al. | |
| 5,877,296 A | 3/1999 | Hamann | |
| 5,959,177 A | 9/1999 | Hein et al. | |
| 6,040,498 A | 3/2000 | Stomp et al. | |
| 6,171,586 B1 | 1/2001 | Lam | |
| 6,194,551 B1 | 2/2001 | Idusogie | |
| 6,248,516 B1 | 6/2001 | Winter et al. | |
| 6,267,958 B1 | 7/2001 | Andya | |
| 6,417,429 B1 | 7/2002 | Hein et al. | |
| 6,420,548 B1 | 7/2002 | Vezina et al. | |
| 6,602,684 B1 | 8/2003 | Umana et al. | |
| 6,630,579 B2 | 10/2003 | Chari | |
| 6,737,056 B1 | 5/2004 | Presta | |
| 6,982,321 B2 | 1/2006 | Winter | |
| 7,087,409 B2 | 8/2006 | Barbas, III | |
| 7,125,978 B1 | 10/2006 | Vezina et al. | |
| 7,332,581 B2 | 2/2008 | Presta | |
| 7,371,826 B2 | 5/2008 | Presta | |
| 7,498,298 B2 | 3/2009 | Doronina | |
| 7,521,541 B2 | 4/2009 | Eigenbrot | |
| 7,527,791 B2 | 5/2009 | Adams | |
| 7,829,674 B2 | 11/2010 | Sabbadini | |
| 9,765,153 B2 | 9/2017 | Brinkmann et al. | |
| 9,925,272 B2 | 3/2018 | Brinkmann et al. | |
| 10,407,511 B2 | 9/2019 | Brinkmann et al. | |
| 10,517,945 B2 | 12/2019 | Benz et al. | |
| 10,519,249 B2 | 12/2019 | Brinkmann et al. | |
| 10,561,737 B2 | 2/2020 | Brinkmann et al. | |
| 10,806,795 B2 | 10/2020 | Brinkmann et al. | |
| 11,273,223 B2 | 3/2022 | Brinkmann et al. | |
| 2002/0164328 A1 | 11/2002 | Shinkawa et al. | |
| 2003/0115614 A1 | 6/2003 | Kanda et al. | |
| 2003/0157108 A1 | 8/2003 | Presta | |
| 2004/0093621 A1 | 5/2004 | Shitara et al. | |
| 2004/0109865 A1 | 6/2004 | Niwa et al. | |
| 2004/0110282 A1 | 6/2004 | Kanda et al. | |
| 2004/0110704 A1 | 6/2004 | Yamane et al. | |
| 2004/0132140 A1 | 7/2004 | Satoh et al. | |
| 2005/0014934 A1 | 1/2005 | Hinton et al. | |
| 2005/0026263 A1 | 2/2005 | Meares | |
| 2005/0059100 A1 | 3/2005 | Meares | |
| 2005/0123546 A1 | 6/2005 | Umana et al. | |
| 2005/0260186 A1 | 11/2005 | Bookbinder et al. | |
| 2006/0025576 A1 | 2/2006 | Miller et al. | |
| 2006/0104968 A1 | 5/2006 | Bookbinder et al. | |
| 2008/0069820 A1 | 3/2008 | Fuh et al. | |
| 2015/0232577 A1 | 8/2015 | Brinkmann et al. | |
| 2015/0238628 A1 | 8/2015 | Brinkmann et al. | |
| 2015/0258209 A1 | 9/2015 | Benz et al. | |
| 2016/0324984 A1* | 11/2016 | Brinkmann | A61K 47/64 |
| 2017/0058050 A1 | 3/2017 | Brinkmann et al. | |
| 2017/0058051 A1 | 3/2017 | Brinkmann et al. | |
| 2020/0164064 A1 | 5/2020 | Benz et al. | |

FOREIGN PATENT DOCUMENTS

| | | |
|---|---|---|
| EA | 018708 B1 | 10/2018 |
| EP | 0404097 A2 | 12/1990 |
| EP | 0425235 B1 | 9/1996 |
| EP | 1870459 A1 | 12/2007 |
| EP | 1798240 B1 | 4/2011 |
| EP | 2319529 A1 | 5/2011 |
| RU | 2396084 C1 | 8/2010 |
| RU | 2509558 C2 | 3/2014 |
| WO | WO199301161 A1 | 1/1993 |
| WO | WO199308829 A1 | 5/1993 |
| WO | WO199316185 A2 | 8/1993 |
| WO | WO199316185 A3 | 9/1993 |
| WO | WO199411026 A2 | 5/1994 |
| WO | WO199411026 A3 | 8/1994 |
| WO | WO199429351 A2 | 12/1994 |
| WO | WO199429351 A3 | 12/1994 |
| WO | WO199627011 A1 | 9/1996 |
| WO | WO199730087 A1 | 8/1997 |
| WO | WO1998050431 A2 | 11/1998 |
| WO | WO1998050431 A3 | 11/1998 |
| WO | WO199858964 A1 | 12/1998 |
| WO | WO199922764 A1 | 5/1999 |
| WO | WO199951642 A1 | 10/1999 |
| WO | WO200050088 A2 | 8/2000 |
| WO | WO200061739 A1 | 10/2000 |
| WO | WO200050088 A3 | 12/2000 |
| WO | WO200129246 A1 | 4/2001 |
| WO | WO200134651 A1 | 5/2001 |
| WO | WO2002031140 A1 | 4/2002 |
| WO | WO2003011878 A2 | 2/2003 |
| WO | WO2003084570 A1 | 10/2003 |
| WO | WO2003085107 A1 | 10/2003 |
| WO | WO2003085119 A1 | 10/2003 |
| WO | WO2003011878 A3 | 11/2003 |
| WO | WO2004056312 A2 | 7/2004 |
| WO | WO2004065569 A2 | 8/2004 |
| WO | WO2004065569 A3 | 8/2004 |
| WO | 2005004809 A2 | 1/2005 |
| WO | WO2005035586 A1 | 4/2005 |
| WO | WO2005035778 A1 | 4/2005 |
| WO | WO2004056312 A3 | 5/2005 |
| WO | WO2005053742 A1 | 6/2005 |
| WO | WO2005100402 A1 | 10/2005 |
| WO | 2005004809 A3 | 2/2006 |
| WO | 2006034488 A2 | 3/2006 |
| WO | WO2006029879 A2 | 3/2006 |
| WO | WO2006044908 A2 | 4/2006 |
| WO | WO2006044908 A3 | 8/2006 |
| WO | 2006034488 A3 | 9/2006 |
| WO | WO2006029879 A3 | 9/2006 |
| WO | WO2007110205 A2 | 10/2007 |
| WO | 2007140371 A2 | 12/2007 |
| WO | WO2007147901 A1 | 12/2007 |
| WO | WO2008002064 A1 | 1/2008 |
| WO | 2007140371 A3 | 2/2008 |
| WO | 2008022349 A2 | 2/2008 |
| WO | WO2007110205 A3 | 2/2008 |
| WO | WO2008077546 A1 | 7/2008 |
| WO | 2008022349 A3 | 11/2008 |
| WO | WO2009007750 A1 | 1/2009 |
| WO | 2009092011 A1 | 7/2009 |
| WO | WO2009080251 A1 | 7/2009 |
| WO | WO2009080252 A1 | 7/2009 |
| WO | WO2009080253 A1 | 7/2009 |
| WO | WO2009080254 A1 | 7/2009 |
| WO | WO2009089004 A1 | 7/2009 |
| WO | WO2009118324 A1 | 10/2009 |
| WO | WO2010056893 A1 | 5/2010 |
| WO | WO2010112193 A1 | 10/2010 |

(56) References Cited

FOREIGN PATENT DOCUMENTS

| WO | WO2010115589 A1 | 10/2010 |
|---|---|---|
| WO | WO2010129304 A2 | 11/2010 |
| WO | WO2010136172 A1 | 12/2010 |
| WO | WO2010145792 A1 | 12/2010 |
| WO | WO2010145793 A1 | 12/2010 |
| WO | WO2011003780 A1 | 1/2011 |
| WO | WO2010129304 A3 | 2/2011 |
| WO | WO201190754 A1 | 7/2011 |
| WO | WO2011090762 A1 | 7/2011 |
| WO | WO2011143545 A1 | 11/2011 |
| WO | 2011156328 A1 | 12/2011 |
| WO | WO2011003557 A8 | 1/2012 |
| WO | WO2012058768 A1 | 5/2012 |
| WO | WO2012093068 A1 | 7/2012 |
| WO | WO2011003557 A1 | 1/2013 |
| WO | WO2013096291 A2 | 6/2013 |
| WO | WO2013096291 A3 | 9/2013 |
| WO | WO2013157953 A1 | 10/2013 |
| WO | WO2013157954 A1 | 10/2013 |
| WO | 2013177062 A2 | 11/2013 |
| WO | 2013177062 A3 | 2/2014 |
| WO | WO2014006124 A1 | 9/2014 |
| WO | WO201501586 * | 7/2015 |
| WO | 2016183104 A1 | 11/2016 |

OTHER PUBLICATIONS

Aigner, A. (2008). "Cellular Delivery In Vivo of Sirna-Based Therapeutics," Curr. Pharm. Des. 14(34):3603-3619.

Akinc, A. et al. (Jul. 2010, e-pub. May 11, 2010). "Targeted Delivery of RNAi Therapeutics With Endogenous and Exogenous Ligand-Based Mechanisms," Mol. Ther. 18(7):1357-1364.

Akinc, A. et al. (May 11, 2010). "Development of Lipidoid-siRNA Formulations For Systemic Delivery to the Liver," Mol. Ther. 17(5):872-879.

Almagro, J. et al. (Jan. 2008). "Humanization of Antibodies," Frontiers in Bioscience 13:1619-1633.

Atwell, S. et al. (1997). "Stable Heterodimers From Remodeling the Domain Interface of a Homodimer Using a Phage Display Library," J. Mol. Biol. 270 (1):26-35.

Baca, M. et al. (Apr. 18, 1997). "Antibody Humanization Using Monovalent Phage Display," J. Biol. Chem. 272 (16):10678-10684.

Baselga, J. (Sep. 2001). "The EGFR As a Target For Anticancer Therapy-Focus On Cetuximab," Eur. J. Cancer 37(Suppl. 4):S16-S22.

Beck, A. et al. (May 2010). "Strategies and Challenges For The Next Generation of Therapeutic Antibodies," Nat. Rev. Immunol. 10(5):345-352.

Bhattarai, S.R. et al. (Dec. 2010, e-pub. Aug. 21, 2010). "Enhanced Gene and siRNA Delivery By Polycation-Modified Mesoporous Silica Nanoparticies Loaded With Chloroquine," Pharm. Res. 27(12):2556-2568, 26 pages.

Brennan, M. et al. (Jul. 5, 1985). "Preparation of Bispecific Antibodies by Chemical Recombination of Monoclonal Immunoglobulin G1 Fragments," Science 229:81-83.

Brinkmann, U. et al. (Oct. 1, 1991). "B3(Fv)-PE38KDEL, a Single-Chain Immunotoxin That Causes Complete Regression of A Human Carcinoma in Mice," Proc. Natl. Acad, Sci. USA 88(19):8616-8620.

Brüggemann, M. et al. (Nov. 1, 1987). "Comparison of the Effector Functions of Human Immunoglobulins Using a Matched Set of Chimeric Antibodies," J. Exp. Med. 166:1351-1361.

Burris, T.P. et al. (Mar. 1999). "A Novel Method For Analysis Of Nuclear Receptor Function At Natural Promoters Peroxisome Proliferator-Activated Receptor Y Agonist Actions on aP2 Gene Expression Detected Using Branched DNA Messenger RNA Quantitation," Mol. Endocrinol. 13(3):410-417.

Carter, P. et al. "Humanization of an Anti-p185HER2 Antibody For Human Cancer Therapy," Proc. Natl. Acad. Sci. USA 89:4285-4289 (May 1992).

Chan, D.P. et al. (Nov. 2013, e-pub. Aug. 7, 2013). "Click Conjugated Polymeric Immuno-Nanoparticles For Targeted siRNA and Antisense Oligonucleotide Delivery," Biomaterials 34(33):8408-8415.

Chari, R.V.J. et al. (Jan. 1, 1992). "Immunoconjugates Containing Noveal maytansinoids: Promissing Anticancer Drugs," Cancer Res. 52:127-131.

Charlton, K.A. (2003)."Expression and Isolation of Recombinant Antibody Fragments in *E. coli*," Chapter 14 in Methods in Molecular Biology, LO, B.K.C. (ed.), Humana Press, Totowa, NJ, 248:245-254.

Chen, Y. et al. (1999). "Selection and Analysis of an Optimized Anti-VEGF Antibody: Crystal Structure of an Affinity-Matured Fab in Complex With Antigen," J Mol. Biol 293:865-881.

Chitnis, M.M. et al. (Oct. 15, 2008). "The Type 1 Insulin-Like Growth Factor Receptor Pathway," Clin. Cancer Res. 14(20):6364-6370.

Chothia, C. et al. (1987). "Canonical Structures for the Hypervariable Regions of Immunoglobulins," J. Mol. Biol. 196:901-917.

Chowdhury, P.S. "Engineering Hot Spots for Affinity Enhancement of Antibodies," Methods Mol. Biol. 207:179-196, (2008).

Clackson, T. et al. (Aug. 15, 1991). "Making antibody fragments using phage display libraries," Nature 352:624-628.

Clynes, R. et al. (Jan. 1998). "Fc Receptors are Required in Passive and Active Immunity to Melanoma," Proc. Natl. Acad, Sci. U.S.A. 95:652-656.

Collins, M.L. et al. (Aug. 1, 1997). "A Branched DNA Signal Amplification Assay for Quantification of Nucleic Acid Targets Below 100 Molecules/ml," Nucleic Acids Res. 25(15):2979-2984.

Cragg et al. (2004). "Antibody Specificity Controls In Vivo Effector Mechanisms of Anti-CD20 Reagents," Blood 103:2738-2743.

Cragg, M.S., et al. (2003). "Complement-Mediated Lysis By Anti-CD20 Mab Correlates With Segregation Into Lipid Rafts," Blood 101:1045-1052.

Cunningham, B.C. et al. (Jun. 2, 1989). "High-Resolution Epitope Mapping of hGH-Receptor Interactions by Alanine-Scanning Mutagenesis," Science 244:1081-1085.

Dall'Acqua, W. et al. (2005). "Antibody Humanization by Framework Shuffling," Methods 36:43-60.

Dubowchik, G.M. et al. (2002). "Doxorubicin Immunoconjugates Containing Bivalent, Lysosomally-Cleavable Dipeptide Linkages," Bioorganic & Medicinal ChemistryLetters 12:1529-1532.

Duncan, A.R. et al. (Apr. 21, 1988). "The Binding Site for C1q on IgG," Nature 322:738-740.

El Ouahabi, A et al. (1999). "Intracellular Visualization ofBrdU-labeled Plasmid DNA/Cationic Liposome Complexes," The Journal of Histochemistry & Cytochemistry 47(9):1159-1166.

Flatman, S. et al. (2007, e-pub. Dec. 11, 2006). "Process analytics for Purification of Monoclonal Antibodies," J. Chromatogr. B. 848:79-87.

Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.

Gerngross, T.U. (Nov. 2004). "Advances in the Production of Human Therapeutic Proteins in Yeasts and Filamentous Fungi," Nature Biotechnology 22(11):1409-1414.

Graham. F.L. et al. (1977). "Characteristics of a Human Celi Line Transformed by DNA from Human Adenovirus Type 5," J. Gen Virol. 36:59-74.

Grote, M. et al. (2012). "Bispecific Antibody Derivatives Based on Full-Length IgG Formats," Methods Mol. Biol. 901:247-263.

Gruber, M. et al. (1994). "Efficient Tumor Cell Lysis Mediated by a Bispecific Single Chain Antibody Expressed in *Escherichia coli*," J. Immunol. 152:5368-5374.

Guyer, R.L. et al. (Aug. 1976). "Immunoglobulin Binding By Mouse Intestinal Epithelial Cell Receptors," J. Immunol. 117(2):587-593.

Haas, A.K. et al. (2012). "Chapter 17: Generation of Fluorescent IgG Fusion Proteins in Mammalian Cells," Methods Mol. Biol. 901:265-276.

Hellstrom, I. et al. (Mar. 1985). "Strong Antitumor Activities of IgG3 Antibodies to a Human Melanoma-associated Ganglioside," Proc. Natl. Acad. Sci. USA 82:1499-1502.

(56) References Cited

OTHER PUBLICATIONS

Hellstrom, I. et al. (Sep. 1986). "Antitumor Effects of L6, an IgG2a Antibody That Reacts With Most Human Carcinomas," Proc. Natl. Acad. Sci. USA 83:7059-7063.
Hinman, L.M. et al. (Jul. 15, 1993). "Preparation and Characterization of Monoclonal Antibody Conjugates of the Calicheamicins: A Novel and Potent Family of Antitumor Antibiotics," Cancer Research 53:3336-3342.
Holliger, P. et al. (Jul. 1993). "'Diabodies'" Small Bivalent and Bispecific Antibody Fragments, Proceedings of the National Academy of Sciences USA 90:6444-6448.
Hoogenboom, H.R. (2002). "Overview of Antibody Phage-Display Technology and its Applications," in Chapter 1 of Methods in Molecular Biology, O'Brien, P.M. (ed.) et al., Humana Press Inc., Totowa, NJ, 178:1-37.
Hudson, P.J. et al. (Jan. 2003). "Engineered Antibodies," Nat. Med. 9(1):129-134.
Idusogie, E.E. et al. (2000). "Mapping of the C1q Binding Site on Rltuxan, a Chimeric Antibody With a Human IgG1 Fc," J. Imrmmol. 164:4178-4184.
International Preliminary Report on Patentability, dated Dec. 27, 2016, for PCT/EP2015/064322, filed Jun. 25, 2015, 7 pages.
International Search Report issued in International Application No. PCT/EP2015/064322, dated Oct. 13, 2015, in 5 pages.
Jeffrey, S.C. et al. (2006, e-pub. Nov. 3, 2005). "Dipeptide-based Highly Potent Doxorubicin Antibody Conjugates," Bioorganic Medicinal Chemistry Letters 16:358-362.
Jhaveri, A.M. et al. (Apr. 25, 2014, e-pub. Apr. 25, 2014). "Multifunctional Polymeric Micelles for Delivery of Drugs and siRNA," Front Pharmacol. 5:77, 26 pages.
Jung, S.H. et al. (May 1994). "Design of Interchain Disulfide Bonds in the Framework Region of the Fv Fragment of the Monoclonal Antibody B3," Proteins 19(1):35-47.
Jérôme, V. et al. (2009). "Exhaustive In Vivo Labelling of Plasmid DNA With BrdU for Intracellular Detection in Non-Viral Transfection of Mammalian Cells," Biotechnology Journal 4(10):1479-1487.
Kabat, E.A. (1991). Sequences of Proteins of Immunological Interest, 5th ed., Public Health Service, National Institutes of Health, Bethesda, MD, pp. 647-723.
Kam, N.W.S. et al. (Aug. 16, 2005). "Carbon Nanotubes as Multifunctional Biological Transporters and Near-Infrared Agents for Selective Cancer Cell Destruction," PNAS 102(33):11600-11605.
Kanda, Y. et al. (2006, e-pub. Apr. 11, 2006). "Comparison of Cell Line for Stable Production of Fucose-Negative Antibodies with Enhanced ADCC," Biotechnol. Bioeng. 94(4):680-688.
Kashmiri, S.V. et al. (2005). "SDR grafting—A New Approach to Antibody Humanization," Methods 36:25-34.
Kies, M.S. et al. (Jul. 2002). "Cetuximab (Imclone/Merck/Bristol-Myers Squibb)," Curr. Opin. Investig. Drugs 3(7):1092-1100.
Kim, J-K. et ai. (1994). "Localization of the Site of the Murine IgGI Molecule That Is Involved in Binding to the Murine Intestinal Fc Receptor," Eur. J. Immunol. 24:2429-2434.
Kindt, T.J. et al. (2007). "Antigens And Antibodies," Chapter 4 in Kuby Immunology 6th Ed., W.H. Freeman and Co., p. 91.
King, H.D. et al. (2002, e-pub. Aug. 14, 2002). "Monoclonal Antibody Conjugates of Doxorubicin with Branched Peptide Linkers: Inhibition of Aggregation by Methoxytriethyleneglycol Chains," J. Med. Chem. 45(19):4336-4343.
Klimka, A. et al. (2000). "Human Ant-CD30 Recombinant Antibodies by Guided Phage Antibody Selection Using Cell Panning," Br. J. Cancer 83(2):252-260.
Kostelny, S.A. et al. (Mar. 1, 1992). "Formation of a Bispecific Antibody By The Use of Leucine Zippers," J. Immunol. 148(5):1547-1553.
Kratz, F. et al. (2006). "Prodrugs of Anthracyclines in Cancer Chemotherapy," Current Medicinal Chemistry 13 (5):477-523.
Lee, S.K. et al. (2012). "Cell-Specific siRNA Delivery By Peptides and Antibodies," Meth. Enzymol. 502:91-122.

Leucuta, S.E. (Apr. 2013). "Systemic and Biophase Bioavallability and Pharmacokinetics of Nanoparticulate Drug Delivery Systems," Curr. Drug. Deliv. 10(2):208-240.
Leus, N.G. et al. (Jan. 1, 2014, e-pub Nov. 12, 2013). "Effective siRNA Delivery to Inflamed Primary Vascular Endothelial Cells by Anti-E-Selectin and Anti-VCAM-1 PEGylated SAINT-Based Lipoplexes," Int. J. Pharm. 459(1-2):40-50.
Li, H. et al. (Feb. 2006; e-published on Jan. 22, 2006). "Optimization of Humanized IgGs in Glycoengineered Pichia pastoris," Nature Biotechnology 24(2):210-215.
Liboska, R. et al. (Dec. 2012). "Most Anti-BrdU Antibodies React with 2'-Deoxy-5-Ethynyluridine—The Method for the Effective Suppression of This Cross-Reactivity," PLOS One 7(12):e51679, 10 pages.
Lode, H.N. et al. (Jul. 15, 1998). "Targeted Therapy with a Novel Enediyene Antibiotic Calicheamicin 011 Effectively Suppresses Growth and Dissemination of Liver Metastases in a Syngeneic Model of Murine Neuroblastoma," Cancer Res. 58:2925-2928.
Malhotra, M. et al. (2013, e-pub. May 21, 2013). "Development and Characterization of Chitosan-PEG-TAT Nanoparticles for the Intracellular Delivery of siRNA.Int." J. Nanomedicine 8:2041-2052.
Mansfield, E. et al. (Sep. 1, 1997). "Recombinant RFB4 Immunotoxins Exhibit Potent Cytotoxic Activity for CD22-Bearing Cells and Tumors," Blood 90(5):2020-2026.
Mather, J.P. (1980). "Establishment and Characterization of Two Distinct Mouse Testicular Epithelial Ceil Lines," Biology of Reproduction 23:243-252.
Mather, J.P. et al. (1982). "Culture of Testicular Cells in Hormone-Supplemented Serum-Free Medium," Annals N.Y. Acad. Sci. 383:44-68.
Merchant, A. M. et al. (Jul. 1998). "An Efficient Route to Human Bispecific IgG," Nature Biotechnology 16:677-681.
Metz, S. et al. (May 17, 2011). "Bispecific Digoxigenin-binding Antibodies for Targeted Payload Delivery," Proc. Natl. Acad. Sci. USA 108(20):8194-8199.
Miele, E. et al. (2012, e-pub. Jul. 20, 2012). "Nanoparticle-Based Delivery Of Small Interfering RNA: Challenges for Cancer Therapy," Int. J. Nanomedicine 7:3637-3657.
Milstein, C. et al. (Oct. 6, 1983). "Hybrid Hybridomas and Their Use In Immunohistochemistry," Nature 305:537-539.
Molina, M.A. et al. (Jun. 15, 2011). "Trastuzumab (herceptin), a Humanized Anti-Her2 Receptor Monoclonal Antibody, Inhibits Basal and Activated Her2 Ectodomain Cleavage In Breast Cancer Ceils," Cancer Res. 61 (12):4744-4749.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Nagy, A. et al. (Jan. 18, 2000). "Stability of Cytotoxic Luteinizing Hormone-Releasing Hormone Conjugate (AN-152) Containing Doxorubicin 14-O-Hemiglutarate in Mouse and Human Serum in Vitro: Implications for the Design of Preclinical Studies," Proc. Nat'l. Acad. Sci. 97(2):829-834.
Neuberger, M.S. (1983). "Expression and Regulation of Immunoglobulin Heavy Chain Gene Transfected into Lymphoid Ceils," The EMBO Journal 2(8):1373-1378.
Okazaki, A. et al. (Mar. 5, 2004). "Fucose Depletion From Human IgG1 Oligosaccharide Enhances Binding Enthalpy and Association Rate Between IgG1 and FcγRIIIa," J. Mol. Biol. 336(5): 1239-1249.
Osbourn, J. et al. (2005). "From Rodent Regents to Human Therapeutics Using Antibody Guided Selection," Methods 36:61-68.
Pace, C.N. et al. (1995). "How to Measure and Predict the Molar Absorption Coefficient of a Protein," Protein Science 4:2411-2423.
Padlan, E.A. (1991). "A Possible Procedure for Reducing the Immunogenicity of Antibody Variable Domains While Preserving their Ligand-Binding Properties," Molecular Immunology 28(4-5):489-498.
Pastan, I. et al. (Jul. 15, 1991). "Characterization of Monoclonal Antibodies B1 and B 3 That React With Mucinous Adenocarcinomas," Cancer Res. 51 (14):3781-3787.
Petkova, S.B. et al. (Oct. 31, 2006). "Enhanced Half-Life of Genetically Engineered Human IgG1 Antibodies in a Humanized FcRn Mouse Model: Potential Application in Humorally Mediated Autoimmune Disease." Int'l. Immunol. 18 (12):1759-1769.

(56) References Cited

OTHER PUBLICATIONS

Picard, D. et al. (Jan. 5, 1984). "A Lymphocyte-specific Enhancer in the Mouse Immunoglobulin K Gene," Nature 307:80-82.
Plückthun, A. (1994). "Antibodies from *Escherichia coli*," in Chapter 11 The Pharmacology of Monoclonal Antibodies, vol. 113, Rosenburg and Moore eds., SpringerVerlag, New York, pp. 269-315.
Portolano, S. et al. (Feb. 1, 1993). "Lack of Promisculty in Autoantigen-Specific H and L Chain Combinations as Revealed by Human H and L Chain 'Roulette'," The Journal of Immunology 150(3):880-887.
Presta, L.G. et al. (Oct. 15, 1997). "Humanization of an Anti-Vascular Endothelial Growth Factor Monoclonal Antibody for the Therapy of Solid Tumors and Other Disorders," Cancer Res. 57:4593-4599.
Presta, L.G. et al. (Sep. 1, 1993). "Humanization of an Antibody Directed Against IgE," J. Immunol. 151 (5):2623-2632.
Queen, C. et al. (Dec. 1989), "A Humanized Antibody That Binds to the Interleukin 2 Receptor," Proc. Natl Acad. Sci. USA 86:10029-10033.
Ravetch, J.V. et al. (1991). "Fc Receptors," Annu. Rev. Immunol. 9:457-492.
Reiter, Y. et al. (Dec. 1995). "Disulfide Stabilization of Antibody Fv: Computer Predictions and Experimental Evaluation," Protein Eng. 8(12):1323-1331.
Reiter, Y. et al. (Oct. 1996). "Engineering Antibody Fv Fragments for Cancer Detection and Therapy: Disulfide-Stabilized Fv Fragments," Nature Biotechnology 14:1239-1245.
Ridgway, J.B.B. et al. (1996). "Knobs-Into-Holes' Engineering of Antibody CH3 Domains for Heavy Chain Heterodimerization," Protein Engineering 9(7):617-621.
Riechmann, L. et al. (Mar. 24, 1988). "Reshaping Human Antibodies for Therapy," Nature 332:323-329.
Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.
Robbins, M. et al. (Jun. 2009). "siRNA and Innate Immunity," Oligonucleotides 19(2):89-102.
Rosok, M.J. et al. (Sep. 13, 1996). "A Combinatorial Library Strategy for the Rapid Humanization of Anticarcinoma BR96 Fab," J. Biol. Chem. 271(37):22611-22618.
Rozema, D.B. et al. (Aug. 7, 2007, e-pub. Jul. 24, 2007). "Dynamic PolyConjugates for Targeted In Vivo Delivery Of siRNA to Hepatocytes," Proc. Natl. Acad. Sci. USA 104(32):12982-12987.
Schneider, B. et al. (2012, e-pub. Sep. 18, 2012). "Targeted siRNA Delivery and mRNA Knockdown Mediated by Bispecific Digoxigenin-binding Antibodies," Mol. Ther. Nucleic Acids 1 :e46, 11 pages.
Semple, S.C. et al. (Feb. 2010, e-pub. Jan. 17, 2010). "Rational Design of Cationic Lipids for siRNA Delivery," Nat. Biotechnol. 28(2):172-176.
Shields, R.L. et al. (Mar. 2, 2001). "High Resolution Mapping of the Binding Site on Human IgG1 for FcγRl, Fcyll, Fcylll, and FcRn and Design of IgG1 Variants With Improved Binding to the FcγR," J. Biol.Chem. 276(9):6591-6604.
Sims, M.J. et al. (Aug. 15, 1993). "A Humanized CD18 Antibody Can Block Function Without Cell Destruction," J. Immunol. 151:2296-2308.
Song, E. et al. (Jun. 2005, e-pub. May 22, 2005). "Antibody Mediated In Vivo Delivery Of Small Interfering Rnas Via Cell-Surface Receptors," Nat. Biotechnol. 23(6):709-717.
Sou, K. et al. (May-Jun. 2000, e-pub. Apr. 14, 2000). "Poly(ethylene glycol)-Modification of the Phospholipid Vesicles by Using The Spontaneous Incorporation of Polyethylene glycol)-Lipid into the Vesicles," Bioconjug. Chem. 11(3):372-379.
Soutschek, J. et al. (Nov. 11, 2004). "Therapeutic Silencing of an Endogenous Gene By Systemic Administration of Modified siRNAs," Nature 432(7014):173-178.
Tao, W. et al. (Sep. 2010. e-pub. Jul. 13. 2010). "Noninvasive Imaging of Lipid Nanoparticle-Mediated Systemic Delivery of Small-Interfering RNA to the Liver," Mol. Ther. 18(9): 1657-1666.

Tiera, M.J. et al. (Oct. 2013). "Polymeric Systems as Nanodevices for siRNA Delivery," Curr. Gene Ther. 13(5):358-369.
Toloue, M.M. et al. (2011). "Chapter 8: Antibody Targeted siRNA Delivery," Methods Mol. Biol. 764:123-139.
Torgov, M.Y. et al. (2005; e-publlshed on Apr. 27, 2005). "Generation of an Intensely Potent Anthracycline by a Monoclonal Antibody-β-Galactosidase Conjugate," Bioconjugate Chem. 16:717-721.
Traunecker, A. et al. (1991). "Bispecific Single Chain Molecules (Janusins) Target Cytotoxic Lymphocytes on HIV Infected Cells," EMBO J. 10(12):3655-3659.
Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.
Urlaub, G. et al. (1980). "Isolation of Chinese hamster cell mutants deficient in dihydrofolate reductase activity," Proc. Natl. Acad. Sci. USA 77(7):4216-4220.
Vitetta, E.S. et al. (Nov. 20, 1987). "Redesigning Nature's Poisons to Create Anti-tumor Reagents," Science 238:1098-1104.
Weidle, U.H. et al. (Jan.-Feb. 2013). "The Intriguing Options of Multispecific Antibody Formats for Treatment of Cancer," Cancer Genomics Proteomics 10(1):1-18.
Wolff, J.A. et al. (Jan. 2008, e-pub. Oct. 23, 2007). "Breaking The Bonds: Non-Viral Vectors Become Chemically Dynamic," Mol. Ther. 16(1):8-15.
Wong, S.C. et al. (Dec. 2012). "Co-Injection of a Targeted, Reversibly Masked Endosomolytic Poiyrner Dramatically Improves the Efficacy of Cholesterol-Conjugated Small Interfering RNAs In Vivo," Nucleic Acid Ther. 22:380-390.
Wright, A. et al. (Jan. 1997). "Effect of Glycosylation on Antibody Function: Implications for Genetics Engineering," Trends Biotechnol. 15:26-32.
Written Opinion of International Searching Authority issued in International Application No. PCT/EP2015/064322, dated Oct. 13, 2015, in 6 pages.
Yamane-Ohnuki, N. et al. (2004, e-pub. Aug. 6, 2004). "Establishment of FUT8 Knockout Chinese hamster Ovary Cells: An Ideal Host Cell Line for Producing Completely Defucosylated Antibodies With Enhances Antibody-Dependent Cellular Cytotoxicity," Biotech. Bioeng. 87:614-622.
Yazaki, P.J. et al. (2004). "Expression of Recombinant Antibodies in Mammalian Cell Lines," Chapter 15 In Methods in Molecular Biology, LO, B.K.C. (ed.), Humana Press, Totowa, NJ, 248:255-268.
Yu, B. et al. (Mar. 2009, e-pub. Mar. 19, 2009). "Targeted Delivery Systems for Oligonucleotide Therapeutics," AAPS J 11(1):195-203.
Zimmermann, T.S. et al. (Mary 4, 2006, e-pub. Mar. 26, 2006). "RNAi-Mediated Gene Silencing in Non-Human Primates," Nature 441 (7089):111-114, 18 pages.
Bagci, H. et al. (May 1993). "Monoclonal Anti-biotin Antibodies Simulate Avidin in the Recognition of Biotin," FEBS 322(1):47-50.
Berger, M. (1975). "Production of Antibodies that Bind Biotin and Inhibit Biotin Containing Enzymes," Biochemistry 14(11):2338-2342.
Cao, Y. et al. (1998). "Development of a Bispecific Monoclonal Antibody as a Universal Immunoprobe For Detecting Biotinylated Macromolecules," Journal of Immunological Methods 220:85-91.
Chowdhury, P.S. (2001). "Targeting Random Mutations to Hotspots in Antibody Variable Domains for Affinity Improvement," Methods in Molecular Biology 178:269-285.
Dakshinamurti, K. et al. (1986). "Production and Characterization of a Monoclonal Antibody to Biotin," Biochem. J. 237:477-482.
De Pascalis, R. et al. (2002). "Grafting of "Abbreviated" Complementarity-Determining Regions Containing Specificity-Determining Residues Essential for Ligand Contact to Engineer A Less Immunogenic Humanized Monoclonal Antibody," Journal of Immunology 169:3076-3084.
Gratzner, H.G. (Oct. 29, 1982). "Monoclonal Antibody to 5-Bromo- and 5-lododeoxyuridine: A New Reagent For Detections of DNA Replication," Science 21 8(4571):474-475.
Kohen, F. et al. (1997). "Preparation and Properties of Anti-biotin Antibodies," Methods Enzymology 279:451-463.

(56) References Cited

OTHER PUBLICATIONS

Léger, O. et al. (Jan. 1, 2011). "Antibody Drug Discovery Chapter 1: Humanization of Antibodies," In Molecular Medicine and Medicinal Chemistry, pp. 1-23.
Maccallum, R.M. et al. (1996). "Antibody-Antigen Interactions: Contact Analysis and Binding Site Topography," Journal of Molecular Biology 262:732-745.
Magaud, J.-P. et al. (1989). "Double Immunocytochemical Labeling of Cell and Tissue Samples With Monoclonal Anti-Bromodeozyuridine," The Journal of Histochemistry and Cytochemistry 37(10): 1517-1527.
Pakula, A.A. et al. (1989). "Genetic Analysis of Protein Stability and Function," Annu. Rev. Genet. 23:289-310.
Rudikoff, S. et al. (Mar. 1982). "Single Amino Acid Substitution Altering Antigen-Binding Specificity," Proc. Natl. Acad. Sci. USA 79:1979-1983.
Vincent, P. et al. (1993). "A Comparison of the Binding of Biotin and Biotinylated Macromolecular Ligands to an Anti-Biotin Monoclonal Antibody and to Streptavidin," Journal of Immunological Methods 165:177-182.
Wark, K.L. et al. (2006: e-pub. May 22, 2006). "Latest Technologies for the Enhancement of Antibody Affinity," Advanced Drug Delivery Reviews 58:657-670.
Williams, D.G. et al. (Jan. 1, 2010). "Chapter 21: Humanising Antibodies by CDR Grafting," In Antibody Engineering 1:319-339.
Wu, H. (2003). "Simultaneous Humanization and Affinity Optimization of Monoclonal Antibodies," Methods In Mol. Biol. 207:197-212.
AvantGen, Inc. (Jul. 27, 2009). "AvantGen's Antibody Humanization and Discovery Technologies-GermlinerTM Antibodies: An Effective and Proprietary Technology for Humanizing Antibodies Based on Epitope-Guided Selection." 4 pages.
Gonzales, N.R. et al. (Jan.-Feb. 2005). "Minimizing the Immunogenicity of Antibodies for Clinical Application," Tumor Biology 26:31-43.
Hwang et al. (May 2005). "Use of Human Germline Genes in a CDR Homology-based Approach to Antibody Humanization," Methods 36(1):35-42.
Feng, J,-M. et al., (2010, e-pub. Jan. 1, 2010), "Receptor-Mediated Transport of Drugs Across the BBB," Neuromethods 45:15-34.
Manich, G. et al. (Jul. 1, 2013). "Study of the Transcytosis of an Anti-Transferrin Receptor Antibody With A Fab' Cargo Across the Blood-Brain Barrier in Mice," European Journal of Pharmaceutical Sciences 49(4):556-564.
Pardridge, W.M. (2008, e-pub. Jul. 16, 2008) "Re-engineering Biopharmaceuticals for Delivery To Brain With Molecular Trojan Horses," Bioconjugate Chemistry 19(7):1327-1338.
Zhou, Q.-H. et al. (Aug. 17, 2011). "Delivery of a Peptide Radiopharmaceutical to Brain with an IgG-Avidin Fusion Protein," Bioconjugate Chemistry 22(8):1611-1618, 21 pages.
Bera et al. (Jan. 1, 1998). "Comparison of Recombinant Immunotoxins Against LeY Antigen Expression Tumor Celis: Influence of Affinity, Size, and Stability," Bioconjugate Chemistry 9(6):736-743.
Hanes, J. et al. (Nov. 1998). "Ribosome Display Efficiently Selects and Evolves High-Affinity Antibodies In vitro From Immune Libraries," Proc. Natl. Acad. Sci. USA 95(24):14130-14135.
Hoffmann, E. et al. (2013, e-pub. Jun. 22, 2013). "PK Modulation of Haptenylated Peptides via Non-Convalent Antibody Complexation," Journal of Controlled Release 171(1):48-56.
Pai, L.H. et al. (Apr. 1, 1991). "Anti-Tumor Activities of Immunotoxins Made of Monoclonal Antibody B3 and Various Forms of Pseudomonas exotoxin," Proc. Natl. Acad. Sci. USA 88:3358-3362.
Zahnd, C. et al. (Apr. 30, 2004). "Directed In Vitro Evolution and Crystallographic Analysis of a Peptide-Binding Single Chain Antibody Fragment (scFv) With Low Picomolar Affinity," Journal of Biological Chemistry 279:18870-18877.
Cravedi, P. et al. (2011, e-pub. Apr. 21, 2011). "Efficacy and Safety of Rituximab Second-Line Therapy for Membranous Nephropathy: A Prospective, Matched-Cohort Study." Am. J. Nephrol. 33:461-468.

FDA (Dec. 2015). "Obinutuzumab (Gazyva)," Natl. Drug Monographs. Retrieved from the internet, https://www.pbm.va.gov/PBM/clinicalguidance/drugmonographs/Obinutuzumab GAZYVA Drug Monograph.pdf, last visited Dec. 16, 2020, 11 pages.
Furie, R. et al. (Nov. 10, 2019). "A Phase II Randomized, Double-Blind, Placebo-Controlled Study to Evaluate the Efficacy and Safety of Obinutuzumab or Placebo in Combination with Mycophenolate Mofetil in Patients with Active Class III or IV Lupus Nephritis," 2019 ACR/ARP Annual Meeting. Abstract No. 939, 3 pages.
International Search Report and Written Opinion, dated Jan. 27, 2021, for PCT Applicant No. PCT/US2020/050072, filed Sep. 10, 2020, 27 pages.
Mendez, L.M.G et al. (Oct. 13, 2018). "Peripheral Blood B Cell Depletion After Rituximab and Complete Response in Lupus Nephritis," Clin. J. Am. Soc. Nephrol. 13:1502-1509.
Reddy, V. et al. (2017, e-pub. Apr. 11, 2017). "Obinutuzumab Induces Superior B-Cell Cytotoxicity To Rituximab in Rheumatoid Arthritis and Systemic Lupus Erythematosus Patient Samples," Rheumatology 16:1227-1237.
Reddy, V. et al. (Jun. 22, 2016). "Optimising B-Cell Depletion in Autoimmune Disease: Is Obinutuzumab the Answer?," Drug Discovery Today 21 (8): 1330-1338, 31 pages.
Reddy, V. et al. (Jun. 9, 2016). "Improving B-Cell Depletion in Rheumatoid Arthritis and Systemic Lupus Erythematosus: Resistance To Rituximab and the Potential of Obinutuzumab," Annals of the Rheumatic Diseases 75(S2):116, 2 pages.
Roche: (Jun. 11, 2019). "Roche's Gazyva (obinutuzumab) Delivers Positive Topline Results For Phase II Lupus nephritis Study," Roche Media Release, 3 pages.
Schindler, T. et al. (Jun. 9, 2016). "Nobility, A Phase 2 Trial to Assess the Safety and Efficacy of Obinutuzumab, A Novel Type 2 Anti-CD20 Monoclonal Antibody (mAB) In Patients (Pts) With ISN/RPS Class III or IV Lupus Nephritis (LN)" Annals of the Rheumatic Diseases AB0423, 75(S2):1051, 1 page.
Experimental Data Showing the KD for the Parental Murine Parental Antibody riled With Petition of Apr. 12, 2016, 2 pages.
Song (2009). "Generation of Multivalent Antibody Against Small Hapten and Studies on Its Bioactivities," 10:1-76, 88 pages. English Abstract.
The Chinese Office Action, dated Oct. 23, 2020, in the related Chinese Appl. No. 201710588836.1, with English Translation, 13 pages.
The Brazilian Office Action, dated Aug. 13, 2020, in the related Brazilian Appl. No. BR112131601495-9, 5 pages.
Experimental Data D19 in Opposition of 13734999.9 (Apr. 12, 2016). Response to the Communication Pursuant to Article 94(3) EPC, 12 pages.
Experimental Report D20 (May 17, 2022). "Experimental Protocol: Determination of the Binding of Murine (m33 KmuM33) and Humanized Antibody (huM33) Binding Site to Biotinylated Payload," 4 pages.
Abhinandan, K.R et al. (Aug. 2008, e-pub. Jul. 9, 2008). "Analysis and improvements To Kabat and Structurally Correct Numbering Of Antibody Variable Domain," Molecular Immunology 45(14):3832-3839.
Berzofsky, J.A et al. (1989). "Nature Of Antigenic Determinants:Haptens," in Immunology 3:47-49, with English Translation.
Bowie, J.U et al. (Mar. 1990). "Deciphering The Message In Protein Sequences; Tolerance To Amino Acid Substitutions," Science 247(4948):1306-1310.
Brown; M. et al. (1996) "Tolerance to Single, but Not Multiple, Amina Acid Replacements in Antibody VH CDR2," J. Immunol. 156:3285-3291.
Burgess, W.H. et al. (Nov. 1990), "Possible Dissociation Of The Heparin-Binding and Mitogenic Activities Of Heparin-Binding (Acidic Fibroblast) Growth Factor-1 From Its Receptor-Binding Activities By Site-Directed Mutagenesis Of A Single Lysine Residue," Journal Of Cell Biology 111:2129-2138.
Caldas, C. et al. (May 2003). "Humanization Of The Anti-CD-18 Antibody 6.7: An Unexptected Effect Of A Framework Residue in Binding To Antigen," Mol. Immunol. 39(15):941 -952. Chang, H.-J

(56) References Cited

OTHER PUBLICATIONS et al. (Jan. 7, 2014). "Loop-Sequence Features and Stability Determines In Antibody Variable Domains By High-Throughput Experiments," Structure 22(1 ):9-21.
Chang, H.-J. et al. (Jan. 7, 2014). "Loop-Sequence Features and Stability Determines in Antibody Variable Dmrnains By High-Thoughput Experiments," Structure 22(1):9-21.
Chen, C. et al. (1995). "Enhancement and Destruction Of Antibody Function By Somatic Mutation: Unequal Occurrence Is Controlled By V Gene Combinatorial Associations," EMBO 14 (12):2784-2794.
Chen, C. et al. (Sep. 1, 1992). "Generation and Analysis Of Random Point Mutations In An Antibody CDR2 Sequence: Many Mutated Antibodies Lose Their Ability To Bind Antigen," J. Exp. Med. 176(3):855-866.
Chien, N.C. et al. (Jul. 1989) "Significant Structural and Functional Change Of An Antigen-Binding Site By A Distant Amino Acid Substitution: Proposal Of A Structural Mechanism," Proc. Natl. Acad. Sci. USA. 86(14):5532-5536.
Coloma, M.J. et al. (Feb. 1997). "Design and Production of Novel Tetravalent Bispecific Antibodies," Nature Biotech 15(2): 159-163.
Dengl, S. et al. (Mar. 2016). "Engineered Hapten-Binding Antibody Derivatives For Modulation Of Pharmacokinetic Properties Of Small Molecules and Targeted Payload Delivery," Immunol. Rev. 270(11:165-177.
Dengl, S. et al. (May 2015; e-pub. Feb. 10, 2015). "Hapten-Directed Spontaneous Disulfide Shuffling: A Universal Technology for Site-Directed Covalent Coupling of Payloads to Antibodies," FASEB J 29(5):1763-1779.
Deyev, S.M. et al. (2009) "Modern Technologies For Creating Synthetic Antibodies For Clinical Application," Acta Nature 1:32-50.
Edwards, B.M. et al. (Nov. 14, 2003). "The Remarkable Flexibility of the Human Antibody Repertoire; Isolation of Over One Thousand Different Antibodies to a Single Protein, Blys," J, Mol. Biol. 334(1):103-118.
Fellouse, F.A. et al. (Aug. 24, 2004). "Synthetic Antibodies From a Four-Amino-Acid Code: A Dominant Role for Tyrosine in Antigen Recognition," Proc. Natl. Acad. Sci. USA 101 (34):12467-12472.
Giusti, A.M. et al., (May 1987). "Somatic Diversification Of S107 From An Antiphosphocholine To An Anti-DNA Autoantibody Is Due To A Single Base Change In its Heavy Chain Variable Region," Proc. Natl. Acad. Sci. USA 84 K9):2926-2930.
Glockshuber, R. et al. (Mar. 26, 1991). "Mapping and Modification Of An Antibody Hapten Binding Site: A Site-Directed Mutagenesis Study of McPC603'" Biochemistry 30(12):3049-3054,.
Guo, H. et al. (Jun. 22, 2004). "Protein Tolerance To Random Amino Acid Change," Proc. Natl. Acad. Sci. USA 101 (25): 9205-9210.
Jorgensen, T.O. et al. (Mar. 2002). "The Antibody Site in Atlantic Salmon: Phage Display and Modeling Of scFv With Anti-Hapten Binding Ability," Dev. Comp. Immunol. 26(2):201-206.
Kanda , P. et al. (Dec. 1995). "Dependence of the Murine Antibody Response to An Anti-CDR2 VH Peptide On Immunogen Formulation," Moi. Immunol. 32:1319-1328.
Klimpel, K.R. et al. (Sep. 1994), "Anthrax Toxin Lethal Factor Contains A Zinc Metaiioprotease Consensus Sequence Which is Required For Lethal Toxin Activity," Mol. Microbiol. 13(6):1093-1100.
Knappik, A. et al., (2000) "Fully Synthetic Human Combinatorial Antibody Libraries (HuCAL) Based on Modular Consensus Frameworks and CDRs Randomized with Trinucleotides," J. Mol. Biol. 296:57-86.
Kussie, P.H. et ai. (1994). "A Single Engineered Amino Acid Substitution Changes Antibody Fine Specificity", J. Immunol. 152:146-152.
Lazar, E. et al. (Mar. 1998). "Transforming Growth Factorcs: Mutation Of Aspartic Acid 47 and Leucine 48 Results In Different Biological Activities," Molecular and Cellular Biology 8(3):1247-1252.

Lloyd, C. et al. (2009, e-pub. Oct. 29, 2008). "Modelling the Human Immune Response: Performance of a 1011 Human Antibody Repertoire Against a Broad Panel of Therapeutically Relevant Antigens," Protein Engineering, Design & Selection 22(3): 159-168.
Luque, L.E. et al. (Nov. 19, 2002, e-pub. Oct. 24, 2002). "A Highly Conserved Arginie Is Critical For The Functional Folding Of Inhibitor Of Apoptosis (IAP) Bir Domains," Biochemistry 41 (46): 13663-1 3671.
Mariuzza, R.A. et al. (1987). "The Structural Basis Of Antigen-Antibody Recognition," Annu. Rev. Biophys. Biophys. Chem. 16:139-159.
Nguyen, V.K. et al. (2000), "Camel Heavy-chain Antibodies: Diverse Germline VHH and Specific Mechanisms Enlarge the Antigen-binding Repertoire," The EMBO Journal 19(5):921-930.
Ohno, S. et al. (May 1985). "Antigen-binding Specificities of Antibodies are Primarily Determined by Seven Residues of VH," Proc. Natl. Acad. Sci. USA 82(9):2945-2949.
Panke, C. et al. (Oct. 2013, e-pub. Aug. 19, 2013). "Quantificatin Of Cell Surface Proteins With Bispecific Antibodies," Protein. Eng. Des. Sei. 26(10):645-654.
Piche-Nicholas, N.M. et al. (2018). "Changes in Complementarity-Determining Regions Significantly Alter IgG Binding to the Neonatal Fc Receptor (FcRn) and Pharmacokinetics," MABS 10(1):81-94.
Qin, X. et al. (Sep. 4, 1998). "Structure-Function Analysis Of The Human Insulin-Like Growth Factor Binding Protein-4," J. Biol. Chem. 273(36):23509-23516.
Schildbach, J.F. et al. (Feb. 1993). "Modulation Of Antibody Affinity By A Non-Contact Residue," Protein Sci, 2(2):206-214.
Schneeweiss, B. et al. (1981). "Gamma-Globulin Prophylaxis," in Immunology, Kiev:Navukova Dumka, p. 141, with English Translation.
Solem, S.T. et al. (Apr. 2004). "The Primary Structure and Specificity Determining Residues Displayed By Recobinant Salomon Antibody Domains," Mol. Immunol. 40(18):1347-1360.
Stancovski, I. et al. (Oct. 1991). "Mechanistic Aspects of the Opposing Effects of Monoclonal Antibodies to the ERBB2 Receptor on Tumor Growth," Proceedings of the National Academy of Science USA 88:8691-8695.
Sun, W.-C. et al. (1997). "Synthesis of Fluorinated Fluoresceins," The Journal of Organic Chemistry 62(19):6469-6475.
Takada, I. et al. (2000). "Alteration Of A Single Amino Acid In Peroxisome Proliferator-Active Receptor-a (PPARa) Generates A PPAR6 Phenotype," Mol. Endocrinol. 14(5)733-740.
Vajdos, F. et al. (2002) "Comprehensive Functional Maps of the Antigen Binding Site of an Anti-ErbB2 Antibody Obtained with Shotgun Scanning Mutagenesis," J. Mol. Biol. 320:415-428.
Vucic, D. et al., (Dec. 18, 1998). "A Mutational Analysis Of The Baculovirus Inhibitor Of Apoptosis Op-IAP," J. Biol. Chem. 273(51):33915-33921.
Winkler, K. et al. (2000). "Changing the Antigen Binding Specificity by Single Point Mutations of an Anti-p24 (HIV-1 antibody", J. Immunol. 165(16):4505-4514.
Wu, H. et al. (1999). "Humanization for a Murine Monoclonal Antibody by Simultaneous Optimization of Framework and CDR Residues," J. Mol. Biol. 19:294(1):151-162.
Yarilin, A.A. (1999). "3: Molecular and Cellular Bases Of Adaptive Immunity," in Fundamentals of Immunology M: Medicine pp. 169-174, with English Translation.
Yasui, H. et al., (1989). "Class Switch From μ To ó Is Mediated By Homologous Recombination Between σ μ and Σ μ Sequences In Human Immunoglobulin Gene Loci.," Eur. J. Immunol. 19:1399-1403.
Yu, C.-M. et al. (Mar. 22, 2012). "Rationalization and Design Of The Complementarity Determining Region Sequences In An Antibody-Antigen Recognition Interface," PloS One 7(3):e33340, pp. 1-15.
Yu, L. et al. (Feb. 2008). "Interaction Between Bevacizumab and Murine VEGF-A: A Reassessment," investigative Opthalmology & Visual Science 49(2):522-527.
Holliger, P. et al. (Sep. 2005) "Engineered Antibody Fragments and The Rise Of Single Domains," Nat. Biotechnol. 23(9): 1126-1136.

* cited by examiner

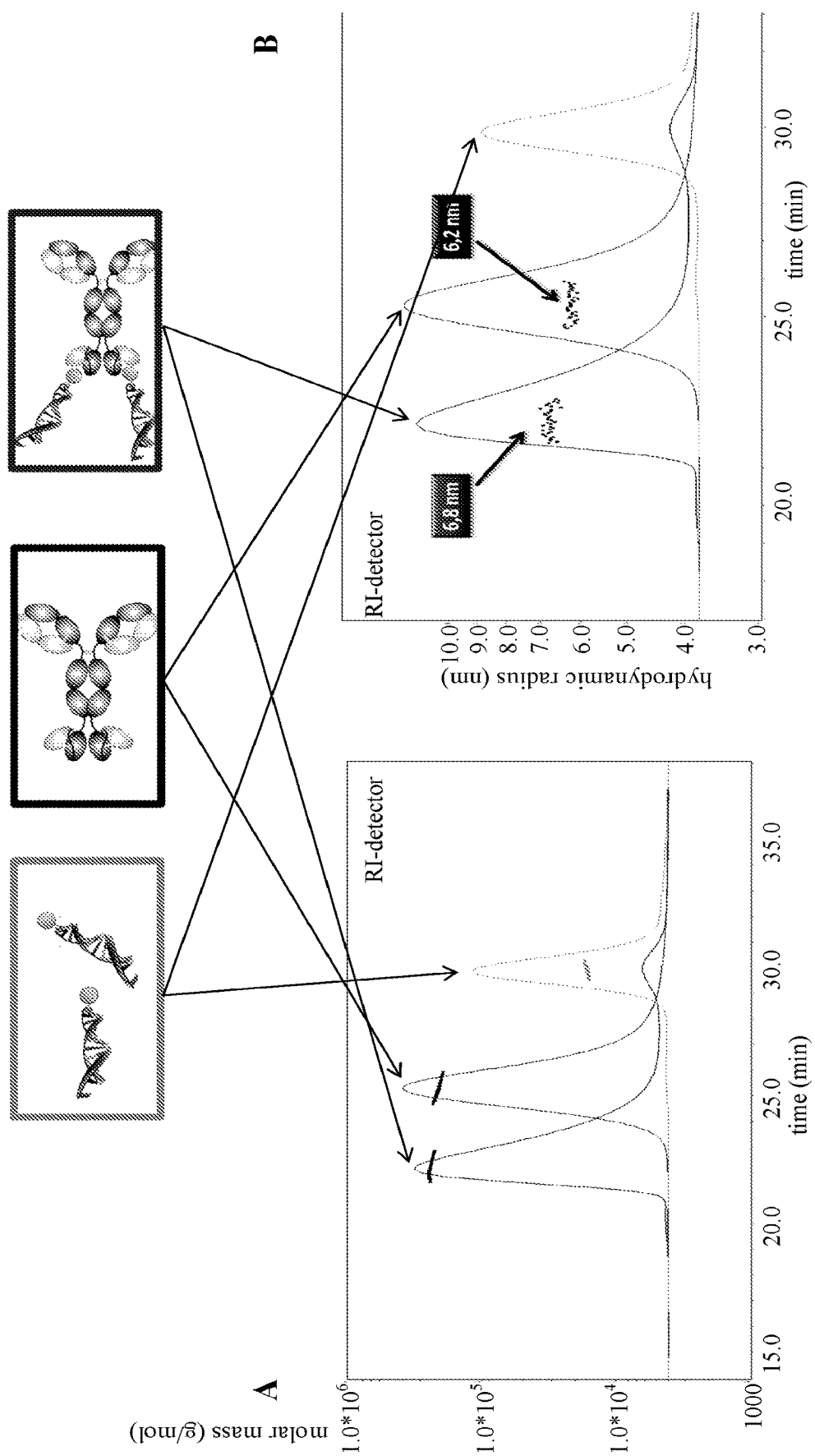

SEQUENCE LISTING

```
<160> NUMBER OF SEQ ID NOS: 14

<210> SEQ ID NO 1
<211> LENGTH: 5
<212> TYPE: PRT
<213> ORGANISM: Mus musculus

<400> SEQUENCE: 1

Glu Tyr Pro Ile His
1               5

<210> SEQ ID NO 2
<211> LENGTH: 10
<212> TYPE: PRT
<213> ORGANISM: Mus musculus

<400> SEQUENCE: 2

Gly Tyr Thr Phe Pro Glu Tyr Pro Ile His
1               5                   10

<210> SEQ ID NO 3
<211> LENGTH: 17
<212> TYPE: PRT
<213> ORGANISM: Artificial Sequence
<220> FEATURE:
<223> OTHER INFORMATION: humanized CDR-H2

<400> SEQUENCE: 3

Gly Ile Val Pro Asn Asn Gly Phe Thr Phe Tyr Ala Gln Lys Leu Gln
1               5                   10                  15

Gly

<210> SEQ ID NO 4
<211> LENGTH: 6
<212> TYPE: PRT
<213> ORGANISM: Mus musculus

<400> SEQUENCE: 4

Val Pro Asn Asn Gly Phe
1               5

<210> SEQ ID NO 5
<211> LENGTH: 10
<212> TYPE: PRT
<213> ORGANISM: Mus musculus
```

<400> SEQUENCE: 5

Lys Asn Leu Gly Ser Ser Pro Leu Asp Tyr
1               5                   10

<210> SEQ ID NO 6
<211> LENGTH: 11
<212> TYPE: PRT
<213> ORGANISM: Mus musculus

<400> SEQUENCE: 6

Arg Ala Ser Gln Ser Ile Gly Thr Ser Ile His
1               5                   10

<210> SEQ ID NO 7
<211> LENGTH: 7
<212> TYPE: PRT
<213> ORGANISM: Mus musculus

<400> SEQUENCE: 7

Tyr Ala Ser Glu Ser Ile Ser
1               5

<210> SEQ ID NO 8
<211> LENGTH: 9
<212> TYPE: PRT
<213> ORGANISM: Mus musculus

<400> SEQUENCE: 8

Gln Gln Ser Asn Arg Trp Pro Leu Thr
1               5

<210> SEQ ID NO 9
<211> LENGTH: 119
<212> TYPE: PRT
<213> ORGANISM: Artificial Sequence
<220> FEATURE:
<223> OTHER INFORMATION: humanized heavy chain variable domain

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Glu Tyr
                20                  25                  30

Pro Ile His Trp Val Arg Gln Ala Pro Gly Gln Gly Leu Glu Trp Met
            35                  40                  45

Gly Gly Ile Val Pro Asn Asn Gly Phe Thr Phe Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Lys Asn Leu Gly Ser Ser Pro Leu Asp Tyr Trp Gly Gln Gly
                100                 105                 110

Thr Thr Val Thr Val Ser Ser
        115

<210> SEQ ID NO 10
<211> LENGTH: 107
<212> TYPE: PRT
<213> ORGANISM: Artificial Sequence
<220> FEATURE:
<223> OTHER INFORMATION: humanized light chain variable domain

<400> SEQUENCE: 10

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Ser
            20                  25                  30

Ile His Trp Tyr Gln Gln Lys Pro Gly Gln Ala Pro Arg Leu Leu Ile
        35                  40                  45

Lys Tyr Ala Ser Glu Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Arg Trp Pro Leu
                85                  90                  95

Thr Leu Gly Gln Gly Thr Lys Leu Glu Ile Lys
            100                 105

<210> SEQ ID NO 11
<211> LENGTH: 119
<212> TYPE: PRT
<213> ORGANISM: Mus musculus

<400> SEQUENCE: 11

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Pro Glu Tyr
            20                  25                  30

Pro Ile His Trp Val Lys Gln Ser His Gly Lys Ser Leu Glu Trp Ile
        35                  40                  45

Gly Gly Ile Val Pro Asn Asn Gly Phe Thr Phe Tyr Asn Gln Lys Phe
    50                  55                  60

Lys Gly Lys Ala Ser Leu Thr Val Asp Lys Ser Ser Thr Ala Tyr
65                  70                  75                  80

Val Glu Val Arg Ser Leu Thr Ser Asp Ser Ala Val Tyr Tyr Cys
                85                  90                  95

Ala Arg Lys Asn Leu Gly Ser Ser Pro Leu Asp Tyr Trp Gly Gln Gly
            100                 105                 110

Thr Thr Leu Thr Val Ser Ser
        115

<210> SEQ ID NO 12
<211> LENGTH: 107
<212> TYPE: PRT
<213> ORGANISM: Mus musculus

<400> SEQUENCE: 12

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln His Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

```
Glu Asp Ile Ala Asp Tyr Tyr Cys Gln Gln Ser Asn Arg Trp Pro Leu
                85                  90                  95
Thr Leu Gly Ala Gly Thr Lys Leu Glu Leu Lys
            100                 105

<210> SEQ ID NO 13
<211> LENGTH: 17
<212> TYPE: PRT
<213> ORGANISM: Artificial Sequence
<220> FEATURE:
<223> OTHER INFORMATION: CDR-H2 variant with Cystein at position 52b/53
      according to Kabat

<400> SEQUENCE: 13

Gly Ile Val Pro Cys Asn Gly Phe Thr Phe Tyr Ala Gln Lys Leu Gln
1               5                   10                  15
Gly

<210> SEQ ID NO 14
<211> LENGTH: 51
<212> TYPE: DNA
<213> ORGANISM: Artificial Sequence
<220> FEATURE:
<223> OTHER INFORMATION: BRDU-DNA conjugate
<220> FEATURE:
<221> NAME/KEY: misc_RNA
<222> LOCATION: (1)..(1)
<223> OTHER INFORMATION: BRDU
<220> FEATURE:
<221> NAME/KEY: misc_feature
<222> LOCATION: (1)..(1)
<223> OTHER INFORMATION: n is a, c, g, or t

<400> SEQUENCE: 14
naccaagcct agagaggagc aatacaacag tacatatcgc gtggtaagcg t           51
```

ANTI-BRDU ANTIBODIES AND METHODS OF USE

CROSS REFERENCE TO RELATED APPLICATIONS

This application is a continuation of U.S. patent application Ser. No. 15/382,329, filed on Dec. 16, 2016, which is a continuation of International Patent Application No. PCT/EP2015/064322, filed on Jun. 25, 2015, which claims priority to European Patent Application No. 14174043.1, filed on Jun. 26, 2014, the entire contents of which are incorporated herein by their references.

SEQUENCE LISTING

The instant application contains a Sequence Listing which has been submitted electronically in ASCII format and is hereby incorporated by reference in its entirety. Said ASCII copy, created on Feb. 26, 2019, is named P32181-US-1-SeqListing.txt and is 6,478 bytes in size.

FIELD OF THE INVENTION

The present invention relates to humanized anti-BRDU antibodies and humanized anti-BRDU derivative antibodies and methods of using the same.

BACKGROUND

Hapten-binding antibodies can be applied as capturing modules for therapeutic and diagnostic applications. For example, hapten-bound entities such as fluorophores, chelating reagents, peptides, nucleic acids, proteins, lipids, nanoparticles, and many other agents can react with hapten-binding antibodies and antibody derivatives. This enables effective detection of such 'payloads', as well as capturing, accumulation at desired locations, crosslinking and other antibody-mediated effects. Since the features and composition of haptens may influence the composition and "behavior" of hapten-bound entities (incl. size, solubility, activity, biophysical properties, PK, biological effects and more), it is highly desired to develop a variety of different hapten-binding entities. Thereby, it is possible to match a selected hapten with a given payload to generate optimized hapten conjugates. Subsequently, optimal hapten-binding entities can be combined with said conjugates to generate optimal antibody-hapten-payload complexes. It is further desired to have hapten-binding entities such as antibody derivatives which are humanized. This enables applications with significantly reduced risk of interference such as immunogenicity in therapeutic applications. The antibodies that are described here bind BRDU as well as BRDU derivatives. These antibodies are termed in this document 'BRDU-binding' or 'anti-BRDU' antibodies.

SUMMARY

The invention provides anti-BRDU antibodies and anti-BRDU-derivative antibodies as well as methods of using the same.

One aspect as reported herein is a humanized anti-BRDU antibody, wherein the antibody comprises (a) a HVR-H1 comprising the amino acid sequence of SEQ ID NO: 01, (b) a HVR-H2 comprising the amino acid sequence of SEQ ID NO: 04, and (c) a HVR-H3 comprising the amino acid sequence of SEQ ID NO: 05. This antibody specifically binds to BRDU.

In one embodiment the antibody has at position 30 of the heavy chain variable domain a proline amino acid residue (numbering according to Kabat).

In one embodiment the antibody has at position 58 of the heavy chain variable domain a phenylalanine amino acid residue (numbering according to Kabat).

In one embodiment the antibody has at position 108 of the heavy chain variable domain a threonine amino acid residue (numbering according to Kabat).

In one embodiment the antibody comprises at position 30 of the heavy chain variable domain the amino acid residue proline, at position 58 of the heavy chain variable domain the amino acid residue phenylalanine and at position 108 of the heavy chain variable domain the amino acid residue threonine (numbering according to Kabat).

In one embodiment the antibody comprises (1) a HVR-H1 comprising the amino acid sequence of SEQ ID NO: 01, (2) at position 30 of the heavy chain variable domain the amino acid reside proline, (3) a HVR-H2 comprising the amino acid sequence of SEQ ID NO: 04, (4) at position 58 of the heavy chain variable domain the amino acid residue phenylalanine, (5) a HVR-H3 comprising the amino acid sequence of SEQ ID NO: 05, and (6) at position 108 of the heavy chain variable domain the amino acid residue tryptophan (numbering according to Kabat).

In one embodiment the antibody comprises a HVR-H1 comprising the amino acid sequence of SEQ ID NO: 02.

In one embodiment the antibody comprises a HVR-H2 comprising the amino acid sequence of SEQ ID NO: 03.

In one embodiment the antibody comprises a HVR-H2 comprising the amino acid sequence of SEQ ID NO: 12.

In one embodiment the antibody further comprises (a) HVR-L1 comprising the amino acid sequence of SEQ ID NO: 06, (b) HVR-L2 comprising the amino acid sequence of SEQ ID NO: 07, and (c) HVR-L3 comprising the amino acid sequence of SEQ ID NO: 08.

In one embodiment the antibody comprises at position 49 of the light chain variable domain the amino acid residue lysine (numbering according to Kabat).

In one embodiment the antibody comprises at position 98 of the light chain variable domain the amino acid residue leucine (numbering according to Kabat).

In one embodiment the antibody comprises at position 49 of the light chain variable domain the amino acid residue lysine and at position 98 of the light chain variable domain the amino acid residue leucine (numbering according to Kabat).

In one embodiment the antibody (1) comprises at position 30 of the heavy chain variable domain the amino acid residue proline, at position 58 of the heavy chain variable domain the amino acid residue phenylalanine and at position 108 of the heavy chain variable domain the amino acid residue threonine, and (2) comprises at position 49 of the light chain variable domain the amino acid residue lysine and at position 98 of the light chain variable domain the amino acid residue leucine (numbering according to Kabat).

In one embodiment the antibody comprises (1) a HVR-H1 comprising the amino acid sequence of SEQ ID NO: 01, (2) at position 30 of the heavy chain variable domain the amino acid reside proline, (3) a HVR-H2 comprising the amino acid sequence of SEQ ID NO: 04, (4) at position 58 of the heavy chain variable domain the amino acid residue phenylalanine, (5) a HVR-H3 comprising the amino acid sequence of SEQ ID NO: 05, (6) at position 108 of the heavy chain variable domain the amino acid residue tryptophan, (7) a HVR-L1 comprising the amino acid sequence of SEQ ID NO: 06, (8) at position 49 of the light chain variable domain the amino acid residue lysine, (9) a HVR-L2 comprising the amino acid sequence of SEQ ID NO: 07, (10) at position 98 of the light chain variable domain the amino acid residue leucine, and (11) a HVR-L3 comprising the amino acid sequence of SEQ ID NO: 08 (numbering according to Kabat).

In one embodiment the antibody comprises (a) a VH sequence having at least 95% sequence identity to the amino acid sequence of SEQ ID NO: 09, (b) a VL sequence having at least 95% sequence identity to the amino acid sequence of SEQ ID NO: 10, or (c) a VH sequence as in (a) and a VL sequence as in (b), wherein (1) at position 30 of the heavy chain variable domain the amino acid residue proline, at position 58 of the heavy chain variable domain the amino acid residue phenylalanine and at position 108 of the heavy chain variable domain the amino acid residue threonine, and (2) comprises at position 49 of the light chain variable domain the amino acid residue lysine and at position 98 of the light chain variable domain the amino acid residue leucine (numbering according to Kabat).

In one embodiment the antibody comprises a VH sequence of SEQ ID NO: 09.

In one embodiment the antibody comprises a VL sequence of SEQ ID NO: 10.

One aspect as reported herein is an antibody comprising a VH sequence of SEQ ID NO: 09 and a VL sequence of SEQ ID NO: 10.

In one embodiment the antibody is a full length IgG1 antibody or a full length IgG4 antibody.

In one embodiment the antibody is a monoclonal antibody.

In one embodiment the antibody is an antibody fragment that binds BRDU.

One aspect as reported herein is a humanized variant of the murine antibody comprising a heavy chain variable domain derived from the amino acid sequence of SEQ ID NO: 11 and a light chain variable domain derived from the amino acid sequence of SEQ ID NO: 12 and which specifically binds to BRDU.

In one embodiment the antibody has at position 30 of the heavy chain variable domain a proline amino acid residue (numbering according to Kabat).

In one embodiment the antibody has at position 58 of the heavy chain variable domain a phenylalanine amino acid residue (numbering according to Kabat).

In one embodiment the antibody has at position 108 of the heavy chain variable domain a threonine amino acid residue (numbering according to Kabat).

In one embodiment the antibody comprises at position 30 of the heavy chain variable domain the amino acid residue proline, at position 58 of the heavy chain variable domain the amino acid residue phenylalanine and at position 108 of the heavy chain variable domain the amino acid residue threonine (numbering according to Kabat).

In one embodiment the antibody comprises at position 49 of the light chain variable domain the amino acid residue lysine (numbering according to Kabat).

In one embodiment the antibody comprises at position 98 of the light chain variable domain the amino acid residue leucine (numbering according to Kabat).

In one embodiment the antibody comprises at position 49 of the light chain variable domain the amino acid residue lysine and at position 98 of the light chain variable domain the amino acid residue leucine (numbering according to Kabat).

In one embodiment the antibody (1) comprises at position 30 of the heavy chain variable domain the amino acid residue proline, at position 58 of the heavy chain variable domain the amino acid residue phenylalanine and at position 108 of the heavy chain variable domain the amino acid residue threonine, and (2) comprises at position 49 of the light chain variable domain the amino acid residue lysine and at position 98 of the light chain variable domain the amino acid residue leucine (numbering according to Kabat).

One aspect as reported herein is a pharmaceutical formulation comprising the antibody as reported herein and a pharmaceutically acceptable carrier.

One aspect as reported herein is the antibody as reported herein for use as a medicament.

One aspect as reported herein is the use of the antibody as reported herein in the manufacture of a medicament.

DESCRIPTION OF THE FIGURE

FIG. 1 A: SEC-MALLS analysis was performed to identify and characterize complexes of anti-TfR/BRDU bispecific antibodies with BRDU-labelled DNA as well as free bispecific antibody and free BRDU-DNA. Complexes elute from the column at a MW of 244.9 kDa, free bispecific antibody is detected at a MW of 215.4 kDa and free BRDU-DNA is detected at a MW of 16.4 kDa.

B: SEC-MALLS analysis was performed to identify and characterize complexes of anti-TfR/BRDU bispecific antibodies with BRDU-labelled DNA as well as free bispecific antibody and free BRDU-DNA. Complexes display a hydrodynamic radius of 6.8 nm, whereas free bispecific antibody displays a hydrodynamic radius of 6.2 nm.

DETAILED DESCRIPTION OF EMBODIMENTS OF THE INVENTION

I. Definitions

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically the Kabat numbering system (see pages 647-660) of Kabat, et al., Sequences of Proteins of Immunological Interest, 5th ed., Public Health Service, National Institutes of Health, Bethesda, Md. (1991) is used for the light chain constant domain CL of kappa and lambda isotype and the Kabat EU index numbering system (see pages 661-723) is used for the constant heavy chain domains (CH1, Hinge, CH2 and CH3).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" denotes the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody denotes an antibody with one or more alterations in one or more hypervariable regions (HVRs), compared to a parent antibody which does not possess such alterations, such alterations resulting in an improvement in the affinity of the antibody for antigen.

The terms "anti-BRDU antibody" and "an antibody that binds to BRDU" refer to an antibody that is capable of binding BRDU with sufficient affinity such that the antibody is useful as a diagnostic and/or therapeutic agent in targeting BRDU.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" denotes a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

The term "chimeric" antibody denotes an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\varepsilon$, $\gamma$, and $\mu$, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents disclosed below.

The term "derived from" denotes that an amino acid sequence is derived from a parent amino acid sequence by introducing alterations at at least one position. Thus, a derived amino acid sequence differs from the corresponding parent amino acid sequence at at least one corresponding position (numbering according to Kabat EU index numbering system for antibody Fc-regions). In one embodiment an amino acid sequence derived from a parent amino acid sequence differs by more than one amino acid residues at corresponding positions from the parent amino acid sequence. In one embodiment an amino acid sequence derived from a parent amino acid sequence differs by more than ten amino acid residues at corresponding positions from the parent amino acid sequence. In one embodiment an amino acid sequence derived from a parent amino acid sequence differs by more than 15 amino acid residues at corresponding positions from the parent amino acid sequence. Thus, the parent amino acid sequence forms the basis for the derived amino acid sequence.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A., et al., Sequences of Proteins of Immunological Interest, 5th ed., Public Health Service, National Institutes of Health, Bethesda, Md. (1991), NIH Publication 91-3242.

"Framework" or "FR" denotes variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody", and "whole antibody" are used herein interchangeably to refer to an antibody having a structure substantially similar to a native antibody structure or having heavy chains that contain an Fc-region as defined herein.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A., et al., Sequences of Proteins of Immunological Interest, 5th ed., Public Health Service, National Institutes of Health, Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized antibody" denotes a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, denotes an antibody that has undergone humanization.

The term "hypervariable region" or "HVR", as used herein, denotes each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia, C. and Lesk, A. M., J. Mol. Biol. 196 (1987) 901-917) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat, E. A., et al., Sequences of Proteins of Immunological Interest, 5th ed. Public Health Service, National Institutes of Health, Bethesda, Md. (1991), NIH Publication 91-3242.) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro, J. C. and Fransson, J., Front. Biosci. 13 (2008) 1619-1633). Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S., et al., J. Chrom. B 848 (2007) 79-87.

An "isolated" nucleic acid denotes a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-BRDU antibody" denotes one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein denotes an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" denotes an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (k), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" denotes a preparation which is in such form as to permit the biological activity of an active ingredient contained therein to be effective, and which contains no additional components which are unacceptably toxic to a subject to which the formulation would be administered.

A "pharmaceutically acceptable carrier" denotes an ingredient in a pharmaceutical formulation, other than an active ingredient, which is nontoxic to a subject., A pharmaceutically acceptable carrier includes, but is not limited to, a buffer, excipient, stabilizer, or preservative.

The term "BRDU", as used herein, denotes bromodeoxyuridine with the chemical formula 5-bromo-2'-deoxyuridine. Other abbreviations are BrdU, BUdR, BrdUrd.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" denotes the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J., et al., Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S., et al., J. Immunol. 150 (1993) 880-887; Clackson, T., et al., Nature 352 (1991) 624-628).

The term "vector", as used herein, denotes a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The term "hapten" denotes a small molecule that can elicit an immune response only when attached to a large carrier such as a protein. Exemplary haptens are aniline, o-, m-, and p-aminobenzoic acid, quinone, hydralazine, halothane, fluorescein, biotin, BRDU, digoxigenin, theophylline and dinitrophenol. In one embodiment the hapten is biotin or digoxigenin or theophylline or carborane or BRDU. In one embodiment the hapten is BRDU.

The term "BRDU that is conjugated to" denotes a BRDU residue which is covalently linked, either directly or indirectly, to a further moiety such as an effector nucleic acid, a polypeptide or a label. In one preferred embodiment the further moiety is a nucleic acid.

The term "covalent complex formation" denotes that after the formation of a non-covalent complex, e.g. between an anti-BRDU antibody and BRDU, a covalent bond is formed between the two partners in the complex. The formation of the covalent bond takes place without the need to add further reactants.

II. Compositions and Methods

In one aspect, the invention is based on humanized antibodies that bind to BRDU. These antibodies are provided herein. Antibodies of the invention are useful, e.g., as monospecific antibodies for the binding of BRDU containing nucleic acids and as multispecific antibodies for the diagnosis or treatment of all kinds of diseases by using the binding specificity to the BRDU containing nucleic acid as universal payloading characteristic of the antibody.

A. Exemplary Anti-BRDU Antibodies

In one aspect, the invention provides isolated antibodies that bind to BRDU. In certain embodiments the anti-BRDU antibodies are humanized anti-BRDU antibodies. In certain embodiments, the anti-BRDU antibodies as reported herein bind to BRDU containing nucleic acids without interfering with the biological activity of the nucleic acid. Therefore these antibodies can be used to improve the pharmacokinetic properties of BRDU containing nucleic acids if the antibody is a monospecific antibody. Also these antibodies can be used for the targeted delivery of a BRDU containing nucleic acids if the antibody is a bi- or multispecific antibody as one binding specificity is directed against BRDU and can be used as universal payloading specificity whereas a second binding specificity specifically binds e.g. to a cell surface molecule and provides for the targeting characteristic/component of the bi- or multispecific antibody.

For the targeted delivery of nucleic acids (i.e. of payload nucleic acids) to or into cells it is desirable to introduce in the payload nucleic acid as few as possible modifications.

By the conjugation of a nucleic acid to polypeptides a significant modification is introduced into in the nucleic acid.

Alternatively the conjugation of a nucleic acid to a non-nucleotide hapten is possible. The modification of the nucleic acid resulting therefrom is less compared to the modification resulting from the conjugation to a polypeptide. But non-nucleotide haptens, such as biotin, digoxigenin, theophylline, fluorescein, are still markedly different from nucleotides, such as e.g. in their structure. Thus, the conjugation to a non-nucleotide hapten can still result in non-tolerable modifications.

It has now been found that a thymidine analogue, i.e. bromodeoxyuridine (BRDU), can be used to provide a hapten that can on the one hand be recognized by an antibody and on the other hand does not introduce significant modification in the payload nucleic acid.

In one aspect, the invention provides an anti-BRDU antibody comprising at least one, two, three, four, five, or six HVRs selected from (a) HVR-H1 comprising the amino acid sequence of SEQ ID NO: 01; (b) HVR-H2 comprising the amino acid sequence of SEQ ID NO: 04; (c) HVR-H3 comprising the amino acid sequence of SEQ ID NO:05; (d) HVR-L1 comprising the amino acid sequence of SEQ ID NO: 06; (e) HVR-L2 comprising the amino acid sequence of SEQ ID NO: 07; and (f) HVR-L3 comprising the amino acid sequence of SEQ ID NO: 08.

In one aspect, the invention provides an anti-BRDU antibody comprising at least one, two, three, four, five, or six HVRs selected from (a) HVR-H1 comprising the amino acid sequence of SEQ ID NO: 02; (b) HVR-H2 comprising the amino acid sequence of SEQ ID NO: 04; (c) HVR-H3 comprising the amino acid sequence of SEQ ID NO:05; (d) HVR-L1 comprising the amino acid sequence of SEQ ID NO: 06; (e) HVR-L2 comprising the amino acid sequence of SEQ ID NO: 07; and (f) HVR-L3 comprising the amino acid sequence of SEQ ID NO: 08.

In one aspect, the invention provides an anti-BRDU antibody comprising at least one, two, three, four, five, or six HVRs selected from (a) HVR-H1 comprising the amino acid sequence of SEQ ID NO: 01; (b) HVR-H2 comprising the amino acid sequence of SEQ ID NO: 03; (c) HVR-H3 comprising the amino acid sequence of SEQ ID NO:05; (d) HVR-L1 comprising the amino acid sequence of SEQ ID NO: 06; (e) HVR-L2 comprising the amino acid sequence of SEQ ID NO: 07; and (f) HVR-L3 comprising the amino acid sequence of SEQ ID NO: 08.

In one aspect, the invention provides an anti-BRDU antibody comprising at least one, two, three, four, five, or six HVRs selected from (a) HVR-H1 comprising the amino acid sequence of SEQ ID NO: 02; (b) HVR-H2 comprising the amino acid sequence of SEQ ID NO: 03; (c) HVR-H3 comprising the amino acid sequence of SEQ ID NO:05; (d) HVR-L1 comprising the amino acid sequence of SEQ ID NO: 06; (e) HVR-L2 comprising the amino acid sequence of SEQ ID NO: 07; and (f) HVR-L3 comprising the amino acid sequence of SEQ ID NO: 08.

In one aspect, the invention provides an anti-BRDU antibody comprising at least one, at least two, or all three VH HVR sequences selected from (a) HVR-H1 comprising the amino acid sequence of SEQ ID NO: 01; (b) HVR-H2 comprising the amino acid sequence of SEQ ID NO: 04; and (c) HVR-H3 comprising the amino acid sequence of SEQ ID NO: 05. In one embodiment, the antibody comprises HVR-H3 comprising the amino acid sequence of SEQ ID NO: 05. In another embodiment, the antibody comprises HVR-H3 comprising the amino acid sequence of SEQ ID NO: 05 and HVR-L3 comprising the amino acid sequence of SEQ ID NO: 08. In a further embodiment, the antibody comprises HVR-H3 comprising the amino acid sequence of SEQ ID NO: 05, HVR-L3 comprising the amino acid sequence of SEQ ID NO: 08, and HVR-H2 comprising the amino acid sequence of SEQ ID NO: 04. In a further embodiment, the antibody comprises (a) HVR-H1 comprising the amino acid sequence of SEQ ID NO: 01; (b) HVR-H2 comprising the amino acid sequence of SEQ ID NO: 04; and (c) HVR-H3 comprising the amino acid sequence of SEQ ID NO: 05.

In another aspect, the invention provides an anti-BRDU antibody comprising at least one, at least two, or all three VL HVR sequences selected from (a) HVR-L1 comprising the amino acid sequence of SEQ ID NO: 06; (b) HVR-L2 comprising the amino acid sequence of SEQ ID NO: 07; and (c) HVR-L3 comprising the amino acid sequence of SEQ ID NO: 08. In one embodiment, the antibody comprises (a) HVR-L1 comprising the amino acid sequence of SEQ ID NO: 06; (b) HVR-L2 comprising the amino acid sequence of SEQ ID NO: 07; and (c) HVR-L3 comprising the amino acid sequence of SEQ ID NO: 08.

In another aspect, an anti-BRDU antibody of the invention comprises (a) a VH domain comprising at least one, at least two, or all three VH HVR sequences selected from (i) HVR-H1 comprising the amino acid sequence of SEQ ID NO: 01, (ii) HVR-H2 comprising the amino acid sequence of SEQ ID NO: 04, and (iii) HVR-H3 comprising an amino acid sequence of SEQ ID NO: 05; and (b) a VL domain comprising at least one, at least two, or all three VL HVR sequences selected from (i) HVR-L1 comprising the amino acid sequence of SEQ ID NO: 06, (ii) HVR-L2 comprising the amino acid sequence of SEQ ID NO: 07, and (c) HVR-L3 comprising the amino acid sequence of SEQ ID NO: 08.

In another aspect, the invention provides an anti-BRDU antibody comprising (a) HVR-H1 comprising the amino acid sequence of SEQ ID NO: 01; (b) HVR-H2 comprising the amino acid sequence of SEQ ID NO: 04; (c) HVR-H3 comprising the amino acid sequence of SEQ ID NO: 05; (d) HVR-L1 comprising the amino acid sequence of SEQ ID NO: 06; (e) HVR-L2 comprising the amino acid sequence of SEQ ID NO: 07; and (f) HVR-L3 comprising an amino acid sequence selected from SEQ ID NO: 08.

In one embodiment, the anti-BRDU antibody is humanized.

It has been found that the humanized anti-BRDU antibody requires at specific position specific residues in order to maintain the characteristics of the non-humanized parental antibody.

The humanized anti-BRDU antibody comprises at Kabat position 30 in the heavy chain variable domain the amino acid residue P.

The humanized anti-BRDU antibody comprises at Kabat position 58 in the heavy chain variable domain the amino acid residue F.

The humanized anti-BRDU antibody comprises at Kabat position 108 in the heavy chain variable domain the amino acid residue T.

In one embodiment, a humanized anti-BRDU antibody comprises HVRs as in any of the above embodiments, and further comprises an acceptor human framework, e.g. a human immunoglobulin framework or a human consensus framework.

In one embodiment, the humanized anti-BRDU antibody comprises a VH comprising HVR-Hs as in any of the above embodiments, and further comprises one or more of the following
    P at position 30 of the heavy chain variable domain, and/or
    F at position 58 of the heavy chain variable domain, and/or
    T at position 108 of the heavy chain variable domain, and/or
    K at position 49 of the light chain variable domain, and/or
    L at position 98 of the light chain variable domain (all positions according to Kabat).

Kabat position 30 of the heavy chain variable domain corresponds to residue number 30 of SEQ ID NO: 09 and 11.

Kabat position 58 of the heavy chain variable domain corresponds to residue number 59 of SEQ ID NO: 09 and 11.

Kabat position 108 of the heavy chain variable domain corresponds to residue number 114 of SEQ ID NO: 09 and 11.

Kabat position 49 of the light chain variable domain corresponds to residue number 49 of SEQ ID NO: 10 and 12.

Kabat position 98 of the light chain variable domain corresponds to residue number 98 of SEQ ID NO: 10 and 12.

These changes (backward mutations) can be introduced to increase the binding affinity of the humanized anti-BRDU antibody.

In another aspect, an anti-BRDU antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 09. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-BRDU antibody comprising that sequence retains the ability to bind to BRDU. In certain embodiments, a total of 1 to 10 amino acids have been substituted, inserted and/or deleted in SEQ ID NO: 09. In certain embodiments, substitutions, insertions, or deletions occur in regions outside the HVRs (i.e., in the FRs). Optionally, the anti-BRDU antibody comprises the VH sequence in SEQ ID NO: 09, including post-translational modifications of that sequence. In a particular embodiment, the VH comprises one, two or three HVRs selected from: (a) HVR-H1 comprising the amino acid sequence of SEQ ID NO: 01 or 02, (b) HVR-H2 comprising the amino acid sequence of SEQ ID NO: 03 or 04, and (c) HVR-H3 comprising the amino acid sequence of SEQ ID NO: 05.

In another aspect, an anti-BRDU antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 10. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-BRDU antibody comprising that sequence retains the ability to bind to BRDU. In certain embodiments, a total of 1 to 10 amino acids have been substituted, inserted and/or deleted in SEQ ID NO: 10. In certain embodiments, the substitutions, insertions, or deletions occur in regions outside the HVRs (i.e., in the FRs). Optionally, the anti-BRDU antibody comprises the VL sequence in SEQ ID NO: 10, including post-translational modifications of that sequence. In a particular embodiment, the VL comprises one, two or three HVRs selected from (a) HVR-L1 comprising the amino acid sequence of SEQ ID NO: 06; (b) HVR-L2 comprising the amino acid sequence of SEQ ID NO: 07; and (c) HVR-L3 comprising the amino acid sequence of SEQ ID NO:08.

In another aspect, an anti-BRDU antibody is provided, wherein the antibody comprises a VH as in any of the embodiments provided above, and a VL as in any of the embodiments provided above. In one embodiment, the antibody comprises the VH and VL sequences in SEQ ID NO: 09 and SEQ ID NO: 10, respectively, including post-translational modifications of those sequences.

In a further aspect of the invention, an anti-BRDU antibody according to any of the above embodiments is a monoclonal antibody, including a chimeric, humanized or human antibody. In one embodiment, an anti-BRDU antibody is an antibody fragment, e.g., an Fv, Fab, Fab', scFv, diabody, or F(ab')2 fragment. In another embodiment, the antibody is a full length antibody, e.g., an intact IgG1 or IgG$_4$ antibody or other antibody class or isotype as defined herein.

In a further aspect, an anti-BRDU antibody according to any of the above embodiments may incorporate any of the features, singly or in combination, as described in Sections 1-5 below:

1. Antibody Affinity

The Kd can be measured by a radiolabeled antigen binding assay (RIA) performed with the Fab version of an antibody of interest and its antigen as described by the following assay. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, Y., et al., J. Mol. Biol. 293 (1999) 865-881). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta, L. G., et al., Cancer Res. 57 (1997) 4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

Alternatively the Kd can be measured using surface plasmon resonance assays using a BIACORE®-2000 or a BIACORE®-3000 or a BIACORE® T-100 (BIAcore, Inc., Piscataway, N.J.). For example, the antigen is immobilized on a CM5 chip at ~10 response units (RU) and the Kd value is determined therewith at 25° C. Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20 µM) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen, Y., et al., J. Mol. Biol. 293 (1999) 865-881. If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson, P. J., et al., Nat. Med. 9 (2003) 129-134. For a review of scFv fragments, see, e.g., Plueckthun, A., In: The Pharmacology of Monoclonal Antibodies, Vol. 113, Rosenburg and Moore (eds.), Springer-Verlag, New York (1994), pp. 269-315; see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J., et al., Nat. Med. 9 (2003) 129-134; and Holliger, P., et al., Proc. Natl. Acad. Sci. USA 90 (1993) 6444-6448. Triabodies and tetrabodies are also described in Hudson, P. J., et al., Nat. Med. 9 (2003) 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison, S. L., et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I., et al., Nature 332 (1988) 323-329; Queen, C., et al., Proc. Natl. Acad. Sci. USA 86 (1989) 10029-10033; U.S. Pat. Nos. 5,821,337; 7,527,791; 6,982,321; 7,087,409; Kashmiri, S. V., et al., Methods 36 (2005) 25-34 (describing SDR (a-CDR) grafting); Padlan, E. A., Mol. Immunol. 28 (1991) 489-498 (describing "resurfacing"); Dall'Acqua, W. F., et al., Methods 36 (2005) 43-60 (describing "FR shuffling"); and Osbourn, J., et al., Methods 36

(2005) 61-68 and Klimka, A., et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J., et al., J. Immunol. 151 (1993) 2296-2308; framework regions derived from the consensus sequence of human antibodies of a particular subgroup of light or heavy chain variable regions (see, e.g., Carter, P., et al., Proc. Natl. Acad. Sci. USA 89 (1992) 4285-4289; and Presta, L. G., et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M., et al., J. Biol. Chem. 272 (1997) 10678-10684 and Rosok, M. J., et al., J. Biol. Chem. 271 (19969 22611-22618).

4. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for BRDU and the other is for any other antigen. In certain embodiments, bispecific antibodies may bind to two different epitopes of BRDU. Bispecific antibodies may also be used to localize cytotoxic agents to cells which express BRDU. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A., et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M., et al., Science 229 (1985) 81-83); using leucine zippers to produce bi-specific antibodies (see, e.g., Kostelny, S. A., et al., J. Immunol. 148 (1992) 1547-1553; using "diabody" technology for making bispecific antibody fragments (see, e.g., Holliger, P., et al., Proc. Natl. Acad. Sci. USA 90 (1993) 6444-6448); and using single-chain Fv (sFv) dimers (see, e.g. Gruber, M., et al., J. Immunol. 152 (1994) 5368-5374); and preparing trispecific antibodies as described, e.g., in Tutt, A., et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to BRDU as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

In one embodiment as reported herein the multispecific antibody as reported herein is a bispecific, bivalent antibody.

In one embodiment the bispecific, bivalent antibody as reported herein is characterized in comprising
a) the heavy chain and the light chain of a first full length antibody that specifically binds to a first antigen, and
b) the modified heavy chain and modified light chain of a second full length antibody that specifically binds to a second antigen, in which the constant domains CL and CH1 are replaced by each other.

The antibodies based on this bispecific, bivalent antibody format are named CrossMabs.

In one embodiment the bispecific, bivalent antibody is characterized in comprising a) the heavy chain and the light chain of a first full length antibody that specifically binds to a first antigen, and
b) the heavy chain and the light chain of a second full length antibody that specifically binds to a second antigen, wherein the N-terminus of the heavy chain is connected to the C-terminus of the light chain via a peptidic linker.

The antibodies based on this bispecific, bivalent antibody format are named one-armed single chain Fabs (OAscFabs).

5. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions". More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |

TABLE 1-continued

| Original Residue | Exemplary Substitutions | Preferred Substitutions |
|---|---|---|
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or SDRs (a-CDRs), with the resulting variant VH or VL being tested for binding affinity. Affinity maturation by constructing and reselecting from secondary libraries has been described, e.g., in Hoogenboom, H. R., et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

One preferred variant is a single cysteine variant wherein the amino acid residue at position 53 according to Kabat in the heavy chain variable domain is cysteine.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 denotes the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A., et al., J. Mol. Biol. 336 (2004) 1239-1249; Yamane-Ohnuki, N., et al., Biotech. Bioeng. 87 (2004) 614-622. Examples of cell lines capable of producing defucosylated antibodies include Lec13 CHO cells deficient in protein fucosylation (Ripka, J., et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N., et al., Biotech. Bioeng. 87 (2004) 614-622; Kanda, Y., et al., Biotechnol. Bioeng. 94 (2006) 680-688; and WO 2003/085107).

Antibodies variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express FcγRI, FcγRII and FcγRIII FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I., et al., Proc. Natl. Acad. Sci. USA 83 (1986) 7059-7063; and Hellstrom, I., et al., Proc. Natl. Acad. Sci. USA 82 (1985) 1499-1502; U.S. Pat. No. 5,821,337 (see Bruggemann, M., et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R., et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H., et al., J. Immunol. Methods 202 (1996) 163-171; Cragg, M. S., et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B., et al., Int. Immunol. 18 (2006) 1759-1769).

Antibodies with reduced effector function include those with substitution of one or more of Fc-region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L., et al., J. Biol. Chem. 276 (2001) 6591-6604).

In certain embodiments, an antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E., et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L., et al., J. Immunol. 117 (1976) 587-593, and Kim, J. K., et al., J. Immunol. 24 (1994) 2429-2434), are described in US 2005/0014934. Those antibodies comprise an Fc-region with one or more substitutions therein which improve binding of the Fc-region to FcRn. Such Fc variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and 5400 (EU numbering) of the heavy chain Fc-region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W., et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

f) Heterodimerization

For the generation of multispecific antibodies it can be necessary to promoter the formation of heterodimeric heavy chain pairings. Several approaches exist for CH3-modifications to enforce the heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. In all such approaches typically the CH3 domain of the first heavy chain and the CH3 domains of the second heavy chain are both engineered in a complementary manner so that each CH3 domain (or the heavy chain comprising it) cannot longer homodimerize with itself but is forced to heterodimerize with the complementary engineered other CH3 domain (so that the first and second CH3 domain (and therewith the first and the second heavy chain) heterodimerize and no homodimers between two first or two second CH3 domains are formed).

These different approaches for improved heavy chain heterodimerization are contemplated as different alternatives in combination with the heavy and/or light chain modifications (VH and VL exchange/replacement in one binding arm and the introduction of substitutions of charged amino acids with opposite charges in the CH1/CL interface) in the multispecific antibodies as reported herein which reduce light chain mispairing and Bence-Jones type side products.

In one preferred embodiment of the invention (in case the multispecific antibody comprises CH3 domains in the heavy chains) the CH3 domains of the multispecific antibody according to the invention is altered by the "knob-into-holes" technology which is described in detail with several examples in e.g. WO 96/027011, Ridgway, J. B., et al., Protein Eng. 9 (1996) 617-621; Merchant, A. M., et al., Nat. Biotechnol. 16 (1998) 677-681; WO 98/050431. In this approach the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield of heterodimer.

Thus in one embodiment the multispecific antibody (comprises a CH3 domain in each heavy chain and) is further characterized in that the first CH3 domain of the first heavy chain of the multispecific antibody and the second CH3 domain of the second heavy chain of the multispecific antibody each meet at an interface which comprises an original interface between the antibody CH3 domains.

wherein said interface is altered to promote the formation of the multispecific antibody, wherein the alteration is characterized in that:

i) the CH3 domain of one heavy chain is altered, so that within the original interface of the CH3 domain of one heavy chain that meets the original interface of the CH3 domain of the other heavy chain within the multispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and ii) the CH3 domain of the other heavy chain is altered, so that within the original interface of the second CH3 domain that meets the original interface of the first CH3 domain within the multispecific antibody an amino acid residue is replaced with an amino acid residue having a smaller side chain volume, thereby generating a cavity within the interface of the second CH3 domain within which a protuberance within the interface of the first CH3 domain is positionable.

Preferably the amino acid residue having a larger side chain volume is selected from the group consisting of arginine (R), phenylalanine (F), tyrosine (Y), tryptophan (W).

Preferably the amino acid residue having a smaller side chain volume is selected from the group consisting of alanine (A), serine (S), threonine (T), valine (V).

In one embodiment both CH3 domains are further altered by the introduction of cysteine (C) as amino acid in the corresponding positions of each CH3 domain such that a disulfide bridge between both CH3 domains can be formed.

In one preferred embodiment, the multispecific antibody comprises the amino acid T366W mutation in the first CH3 domain of the "knobs chain" and the amino acid T366S, L368A, Y407V mutations in the second CH3 domain of the "hole chain". An additional interchain disulfide bridge between the CH3 domains can also be used (Merchant, A. M., et al., Nature Biotech. 16 (1998) 677-681) e.g. by introducing the amino acid Y349C mutation into the CH3 domain of the "hole chain" and the amino acid E356C mutation or the amino acid S354C mutation into the CH3 domain of the "knobs chain".

In one preferred embodiment, the multispecific antibody (which comprises a CH3 domain in each heavy chain) comprises the amino acid S354C, T366W mutations in one of the two CH3 domains and the amino acid Y349C, T366S, L368A, Y407V mutations in the other of the two CH3 domains (the additional amino acid S354C mutation in one CH3 domain and the additional amino acid Y349C mutation in the other CH3 domain forming an interchain disulfide bridge) (numbering according to Kabat).

Other techniques for CH3-modifications to enforcing the heterodimerization are contemplated as alternatives and described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment the heterodimerization approach described in EP 1 870 459 A1, is used. This approach is based on the introduction of substitutions/mutations of charged amino acids with the opposite charge at specific amino acid positions in the CH3/CH3 domain interface between both heavy chains. In one preferred embodiment the multispecific antibody comprises the amino acid R409D, K370E mutations in the CH3 domain of the first heavy chain (of the multispecific antibody) and the amino acid D399K, E357K mutations in the seconds CH3 domain of the second heavy chain (of the multispecific antibody) (numbering according to Kabat).

In another embodiment the multispecific antibody comprises the amino acid T366W mutation in the CH3 domain of the "knobs chain" and the amino acid T366S, L368A, Y407V mutations in the CH3 domain of the "hole chain" and additionally the amino acid R409D, K370E mutations in the CH3 domain of the "knobs chain" and the amino acid D399K, E357K mutations in the CH3 domain of the "hole chain".

In another embodiment the multispecific antibody comprises the amino acid S354C, T366W mutations in one of the two CH3 domains and the amino acid Y349C, T366S, L368A, Y407V mutations in the other of the two CH3 domains or the multispecific antibody comprises the amino acid Y349C, T366W mutations in one of the two CH3 domains and the amino acid S354C, T366S, L368A, Y407V mutations in the other of the two CH3 domains and additionally the amino acid R409D, K370E mutations in the CH3 domain of the "knobs chain" and the amino acid D399K, E357K mutations in the CH3 domain of the "hole chain".

In one embodiment the heterodimerization approach described in WO2013/157953 is used. In one embodiment the first CH3 domain comprises the amino acid T366K mutation and the second CH3 domain comprises the amino acid L351D mutation. In a further embodiment the first CH3 domain further comprises the amino acid L351K mutation. In a further embodiment the second CH3 domain further comprises an amino acid mutation selected from Y349E, Y349D and L368E (preferably L368E).

In one embodiment the heterodimerization approach described in WO2012/058768 is used. In one embodiment the first CH3 domain comprises the amino acid L351Y, Y407A mutations and the second CH3 domain comprises the amino acid T366A, K409F mutations. In a further embodiment the second CH3 domain comprises a further amino acid mutation at position T411, D399, S400, F405, N390 or K392 e.g. selected from a) T411N, T411R, T411Q, T411K, T411D, T411E or T411W, b) D399R, D399W, D399Y or D399K, c) S400E, S400D, S400R or S400K, F405I, F405M, F405T, F405S, F405V or F405W, N390R, N390K or N390D, K392V, K392M, K392R, K392L, K392F or K392E. In a further embodiment the first CH3 domain comprises the amino acid L351Y, Y407A mutations and the second CH3 domain comprises the amino acid T366V, K409F mutations. In a further embodiment the first CH3 domain comprises the amino acid Y407A mutation and the second CH3 domain comprises the amino acid T366A, K409F mutations. In a further embodiment the second CH3 domain further comprises the amino acid K392E, T411E, D399R and S400R mutations.

In one embodiment the heterodimerization approach described in WO2011/143545 is used e.g. with the amino acid modification at a position selected from the group consisting of 368 and 409.

In one embodiment the heterodimerization approach described in WO2011/090762 is used, which also uses the knobs-into-holes technology described above. In one embodiment the first CH3 domain comprises the amino acid T366W mutation and the second CH3 domain comprises the amino acid Y407A mutation. In one embodiment the first CH3 domain comprises the amino acid T366Y mutation and the second CH3 domain comprises the amino acid Y407T mutation.

In one embodiment the multispecific antibody is of IgG2 isotype and the heterodimerization approach described in WO2010/129304 is used.

In one embodiment the heterodimerization approach described in WO2009/089004 is used. In one embodiment the first CH3 domain comprises the substitution of the amino acid residue K392 or N392 with a negative-charged amino acid (e.g. glutamic acid (E), or aspartic acid (D), preferably K392D or N392D) and the second CH3 domain comprises the substitution of the amino acid residue D399, E356, D356 or E357 with a positive-charged amino acid (e.g. Lysine (K) or arginine (R), preferably D399K, E356K, D356K, or E357K and more preferably D399K and E356K). In a further embodiment the first CH3 domain further comprises substitution of the amino acid residue K409 or R409 with a negative-charged amino acid (e.g. glutamic acid (E), or aspartic acid (D), preferably K409D or R409D). In a further embodiment the first CH3 domain further or alternatively comprises substitution of the amino acid residue K439 and/or K370 with a negative-charged amino acid (e.g. glutamic acid (E), or aspartic acid (D)).

In one embodiment the heterodimerization approach described in WO2007/147901 is used. In one embodiment the first CH3 domain comprises the amino acid K253E, D282K, and K322D mutations and the second CH3 domain comprises the amino acid D239K, E240K, and K292D mutations.

In one embodiment the heterodimerization approach described in WO2007/110205 is used.

B. Anti-BRDU Antibody Nucleic Acid Complexes siRNAs and Hapten-Containing siRNA Derivatives The general principles of siRNA design and construction are known to a person skilled in the art and will not be considered here in detail.

An important feature of our modular targeting approach is the linkage of the siRNA to haptens or to a hapten-containing moiety without compromising either the siRNA functionality or the interaction between the hapten and the hapten-binding domain of the bsAb (bispecific antibody).

For direct coupling of hapten to the siRNA of choice, it has been selected the 3' end of the sense strand of double-stranded siRNA derivatives. This position in siRNA was previously found to tolerate added entities (such as cholesterol (25)) without affecting siRNA activity. In accordance with this, it has been observed that the potency of 3'-hapten-conjugated siRNA derivatives, i.e. their ability to reduce target mRNA levels, to be the same as unmodified siRNA (13). As an additional modification, fluorescent compounds such as Cy5 can be attached to the 5' end of the sense strand to enable visualization and tracking of siRNA (e.g. Dig-siRNA-Cy5). Hapten coupling to the 5' end of the sense strand also yields siRNA with good activity in our experience, but is not superior to coupling to the 3' end.

Hapten-Containing Nanoparticles

Hapten-coupled siRNA can directly be complexed with bsAbs. These complexes are able to deliver siRNA specifically to cells which express the respective target antigen on their surface. However, specific accumulation of siRNA on and in intracellular vesicles (upon internalization) by itself does in most cases not result in specific gene knock-down. The reason for this is that unmodified siRNA accumulates in endosomal compartments but does not escape into the cytoplasm (13). In order to enable delivery into the cytosol, the siRNA can be packaged into nanoparticles (1,2,26,27,3, 28,29,30,5,31,32,9) which carry haptens on their surface. These haptens need to be accessible to bsAbs when incorporated into the structure of the (large) nanoparticle. Various kinds of nanoparticles for effective siRNA delivery have been described, many of which contain PEG. Therefore, one way of generating hapten-containing nanoparticles is the application of hapten-coupled PEG derivatives as components for nanoparticle generation. Incorporation of these reagents into formulations generates hapten-decorated nanoparticles (e.g. siRNA in Dig-LNP). Hapten-decorated nanoparticles can in some instances also be generated by formulating hapten-coupled siRNAs into standard nanoparticles. Surprisingly, this results in nanoparticles which have hapten molecules exposed on their surface in an antibody-accessible way. Fluorescently labelled siRNA can be incorporated into hapten-decorated nanoparticles in the same manner without loss of the fluorescent signal. This can be used for visualization and tracking of hapten-containing bsAb-targeted nanoparticles.

Two established types of nanoparticles are dynamic polyconjugates (DPCs) and lipid-based nanoparticles (LNPs). DPCs and LNPs containing hapten-conjugated PEG lipids have been used for the construction of functional siRNA moieties for cellular targeting (13). DPCs include scaffold-reagents, like poly butyl and amino vinyl ether (PBAVE), an endosomolytic polymer that is shielded from non-specific cell interactions by reversible covalent modification with polyethylene glycol (PEG). Both siRNA and hapten can be attached to the polymer by linkers which are either stable (e.g. for hapten linkage) or which enable pH dependent payload release (30, 32, 33).

Hapten-decorated DPCs can be complexed with bsAb at a defined molar ratio (e.g. 1:1 or 2:1) to generate bsAb-targeted DPCs. Loading of bsAbs with siRNA containing DPCs results in an increase in molecular weight and hydrodynamic radius which can be detected by SEC-MALLS. For instance, Dig-polymer-siRNA DPCs without bsAb are a poly-disperse solution with molecules of an estimated molecular weight between 300-720 kDa and a hydrodynamic radius from 7-10 nm. Addition of bsAb to form hapten-polymer-siRNA DPC-bsAb complexes increases the molecular weight range to 500-1100 kDa and the hydrodynamic radius to 9-12.5 nm (13).

LNPs contain polyethylene glycol (PEG)-lipids whose lipophilic acyl chains anchor the hydrophilic PEG molecules in the particle. This ensures particle stability and structural integrity. The acyl chains of the PEG-lipids can be of various lengths. The LNPs which we have successfully used contain PEG-lipids either with a relatively long C18 anchor that consist of 18 methandiyl groups and is considered non-exchangeable, or with a shorter C16 anchor that consists of 16 methandiyl groups and is highly exchangeable (34,35). Hapten-conjugated siRNA-containing LNPs alone or complexed with the bsAb in PBS can be analyzed by dynamic light scattering (DLS) to determine their hydrodynamic radii and poly-dispersity indices (Pdi). LNPs can be incubated together with bsAbs at room temperature (~25° C.; up to 3 hours), and the time-course of change in particle size and poly-dispersity can be determined by DLS (13, 36).

Hapten-decorated LNP formulations which were successfully used by us contained a total of 1.4 mol % PEG-lipids, of those were 0.4 or 0.04 mol % hapten-coupled (Dig-modified) C18 PEG-lipids. The remaining hapten-free PEG-lipids contained C16 lipid-anchors to enable effective LNP-de-shielding and high siRNA transfer/transfection potency (34, 35, and 36). Using such LNPs, a knockdown efficiency of up to 90% knockdown with IC50 of 1.7 nM has been achieved. Moreover, in contrast to results obtained with other siRNA formulations (37), any immunostimulatory effects with these LNPs were not observed (13).

CITED DOCUMENTS

1. Akinc, A., et al. Mol. Ther. 18 (2010) 1357-1364.
2. Bhattarai, S. R., et al., Pharm. Res. 27 (2010) 2556-2568.
3. Lee, S. K., et al., Meth. Enzymol. 502 (2012) 91-122.
4. Leus, N. G., et al., Int. J. Pharm. 459 (2014) 40-50.
5. Semple, S. C., et al., Nat. Biotechnol. 28 (2010) 172-176.
6. Song, E., et al., Nat. Biotechnol. 23 (2005) 709-717.
7. Toloue, M. M. and Ford, L. P., Methods Mol. Biol. 764 (2011) 123-139.
8. Yu, B., et al., AAPS J 11 (2009) 195-203.
9. Zimmermann, T. S., et al., Nature 441 (2006) 111-114.
10. Beck, A., et al., Nat. Rev. Immunol. 10 (2010) 345-352.
11. Weidle, U. H., et al., Cancer Genomics Proteomics 10 (2013) 1-18.
12. Metz S., et al., Proc. Natl. Acad. Sci. USA 108 (2011) 8194-8199.
13. Schneider, B., et al., Mol. Ther. Nucleic Acids. 1 (2012) e46.
14. Jung, S. H., et al., Proteins 19 (1994) 35-47.
15. Reiter, Y., et al., Protein Eng. 8 (1995) 1323-1331.
16. Reiter, Y., et al., Nat. Biotechnol. 14 (1996) 1239-1245.
17. Ridgway, J. B., et al., Protein Eng. 9 (1996) 617-621.
18. Molina, M. A., et al., Cancer Res. 61 (2001) 4744-4749.
19. Baselga, J., Eur. J. Cancer 37 (2001) Suppl. 4, S16-S22.
20. Kies, M. S. and Harari, P. M., Curr. Opin. Investig. Drugs 3 (2002) 1092-1100.

21. Chitnis, M. M., et al., Clin. Cancer Res. 14 (2008) 6364-6370.
22. Mansfield, E., et al., Blood 90 (1997) 2020-2026.
23. Brinkmann, U., et al., Proc. Natl. Acad. Sci. USA 88 (1991) 8616-8620.
24. Pastan, I., et al., Cancer Res. 51 (1991) 3781-3787.
25. Soutschek, J., et al., Nature 432 (2004) 173-178.
26. Chan, D. P., et al., Biomaterials 34 (2013) 8408-8415.
27. Jhaveri, A. M. and Torchilin, V. P., Front Pharmacol. 5 (2014) 77.
28. Malhotra, M., et al., Int. J. Nanomedicine 8 (2013) 2041-2052.
29. Miele E., et al., Int. J. Nanomedicine 7 (2012) 3637-3657.
30. Rozema, D. B., et al., Proc. Natl. Acad. Sci. USA 104 (2007) 12982-12987.
31. Tiera, M. J., et al., Curr. Gene Ther. 13 (2013) 358-369.
32. Wolff, J. A. and Rozema, D. B., Mol. Ther. 16 (2008) 8-15.
33. Wong, S. C., et al., Nucleic Acid Ther. 22 (2012) 380-390.
34. Akinc, A., et al., Mol. Ther. 17 (2009) 872-879.
35. Sou, K., et al., Bioconjug. Chem. 11 (2000) 372-379.
36. Tao, W., et al., Mol. Ther. 18 (2010) 1657-1666.
37. Robbins, M., et al., Oligonucleotides 19 (2009) 89-102.
38. Grote, M., et al., Methods Mol. Biol. 901 (2012) 247-263.
39. Haas, A. K., et al., Methods Mol. Biol. 901 (2012) 265-276.
40. Aigner, A., Curr. Pharm. Des. 14 (2008) 3603-3619.
41. Leucuta, S. E., Curr. Drug. Deliv. 10 (2013) 208-240.
42. Burris, T. P., et al., Mol. Endocrinol. 13 (1999) 410-417.
43. Collins, M. L., et al., Nucleic Acids Res. 25 (1997) 2979-2984.

C. Recombinant Methods and Compositions

Antibodies may be produced using recombinant methods and compositions, e.g., as described in U.S. Pat. No. 4,816,567. In one embodiment, isolated nucleic acid encoding an anti-BRDU antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., YO, NSO, Sp20 cell). In one embodiment, a method of making an anti-BRDU antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-BRDU antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H., et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177; 6,040,498; 6,420,548; 7,125,978; 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L., et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P., et al., Annals N.Y. Acad. Sci. 383 (1982) 44-68; MRC 5 cells; and FS4 cells. Other useful mammalian host cell lines include Chinese hamster ovary (CHO) cells, including DHFR$^-$ CHO cells (Urlaub, G., et al., Proc. Natl. Acad. Sci. USA 77 (1980) 4216-4220); and myeloma cell lines such as YO, NSO and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

D. Assays

Anti-BRDU antibodies provided herein may be identified, screened for, or characterized for their physical/chemical properties and/or biological activities by various assays known in the art.

Binding Assays and Other Assays

In one aspect, an antibody of the invention is tested for its antigen binding activity, e.g., by known methods such as ELISA, Western blot, etc.

In another aspect, competition assays may be used to identify an antibody that competes with the antibodies as reported herein for binding to BRDU.

In an exemplary competition assay, immobilized BRDU is incubated in a solution comprising a first labeled antibody that binds to BRDU and a second unlabeled antibody that is being tested for its ability to compete with the first antibody for binding to BRDU. The second antibody may be present in a hybridoma supernatant. As a control, immobilized BRDU is incubated in a solution comprising the first labeled antibody but not the second unlabeled antibody. After incubation under conditions permissive for binding of the first antibody to BRDU, excess unbound antibody is removed, and the amount of label associated with immobilized BRDU is measured. If the amount of label associated with immobilized BRDU is substantially reduced in the test sample relative to the control sample, then that indicates that the second antibody is competing with the first antibody for binding to BRDU. See Harlow, E. and Lane, D., Antibodies: A Laboratory Manual, Chapter 14, Cold Spring Harbor Laboratory, Cold Spring Harbor, N.Y. (1988).

E. Immunoconjugates

The invention also provides immunoconjugates comprising an anti-BRDU antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296); Hinman, L. M., et al., Cancer Res. 53 (1993) 3336-3342; and Lode, H. N., et al., Cancer Res. 58 (1998) 2925-2928); an anthracycline such as daunomycin or doxorubicin (see Kratz, F., et al., Curr. Med. Chem. 13 (2006) 477-523; Jeffrey, S. C., et al., Bioorg. Med. Chem. Lett. 16 (2006) 358-362; Torgov, M. Y., et al., Bioconjug. Chem. 16 (2005) 717-721; Nagy, A., et al., Proc. Natl. Acad. Sci. USA 97 (2000) 829-834; Dubowchik, G. M., et al., Bioorg. & Med. Chem. Letters 12 (2002) 1529-1532; King, H. D., et al., J. Med. Chem. 45 (20029 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the trichothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S., et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V., et al., Cancer Res. 52 (1992) 127-131; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

F. Methods and Compositions for Diagnostics and Detection

The term "detecting" as used herein encompasses quantitative or qualitative detection.

In one embodiment, an anti-BRDU antibody for use in a method of diagnosis or detection is provided. Such method may be an in vitro or in vivo method.

In certain embodiments, labeled anti-BRDU antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited, $^3H$, to, the radioisotopes $^{32}P$, $^{14}C$, $^{125}I$, $^3H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, BRDU/avidin, spin labels, bacteriophage labels, stable free radicals, and the like.

G. Pharmaceutical Formulations

Pharmaceutical formulations of an anti-BRDU antibody as described herein are prepared by mixing such antibody having the desired degree of purity with one or more optional pharmaceutically acceptable carriers (Osol, A. (ed.) Remington's Pharmaceutical Sciences, 16th edition (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

H. Therapeutic Methods and Compositions

Any of the anti-BRDU antibodies provided herein may be used in therapeutic methods.

In one aspect, an anti-BRDU antibody for use as a medicament is provided. In certain embodiments, an anti-BRDU antibody for use in a method of treatment is provided.

In a further aspect, the invention provides for the use of an anti-BRDU antibody in the manufacture or preparation of a medicament.

In a further aspect, the invention provides pharmaceutical formulations comprising any of the anti-BRDU antibodies provided herein. In one embodiment, a pharmaceutical formulation comprises any of the anti-BRDU antibodies provided herein and a pharmaceutically acceptable carrier.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 mg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 mg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. The progress of this therapy is easily monitored by conventional techniques and assays.

It is understood that any of the above formulations or therapeutic methods may be carried out using an immunoconjugate of the invention in place of or in addition to an anti-BRDU antibody.

III. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-BRDU antibody.

IV. Specific Embodiments

1. A humanized anti-BRDU antibody, wherein the antibody comprises (a) HVR-H1 comprising the amino acid sequence of SEQ ID NO: 01, (b) HVR-H2 comprising the amino acid sequence of SEQ ID NO: 04, and (c) HVR-H3 comprising the amino acid sequence of SEQ ID NO: 05.
2. A humanized anti-BRDU antibody, wherein the antibody comprises (a) HVR-H1 comprising the amino acid sequence of SEQ ID NO: 02, (b) HVR-H2 comprising the amino acid sequence of SEQ ID NO: 04, and (c) HVR-H3 comprising the amino acid sequence of SEQ ID NO: 05.
3. A humanized anti-BRDU antibody, wherein the antibody comprises (a) HVR-H1 comprising the amino acid sequence of SEQ ID NO: 01, (b) HVR-H2 comprising the amino acid sequence of SEQ ID NO: 03, and (c) HVR-H3 comprising the amino acid sequence of SEQ ID NO: 05.
4. A humanized anti-BRDU antibody, wherein the antibody comprises (a) HVR-H1 comprising the amino acid sequence of SEQ ID NO: 02, (b) HVR-H2 comprising the amino acid sequence of SEQ ID NO: 03, and (c) HVR-H3 comprising the amino acid sequence of SEQ ID NO: 05.
5. A humanized anti-BRDU antibody, wherein the antibody comprises (a) HVR-H1 comprising the amino acid sequence of SEQ ID NO: 01, (b) HVR-H2 comprising the amino acid sequence of SEQ ID NO: 13, and (c) HVR-H3 comprising the amino acid sequence of SEQ ID NO: 05.
6. A humanized anti-BRDU antibody, wherein the antibody comprises (a) HVR-H1 comprising the amino acid sequence of SEQ ID NO: 02, (b) HVR-H2 comprising the amino acid sequence of SEQ ID NO: 13, and (c) HVR-H3 comprising the amino acid sequence of SEQ ID NO: 05.
7. The humanized anti-BRDU antibody according to any one of embodiments 1 to 6 further comprising (a) HVR-L1 comprising the amino acid sequence of SEQ ID NO: 06, (b) HVR-L2 comprising the amino acid sequence of SEQ ID NO: 07, and (c) HVR-L3 comprising the amino acid sequence of SEQ ID NO: 08.
8. The humanized anti-BRDU antibody according to any one of embodiments 1 to 7, wherein the antibody has at position 30 of the heavy chain a proline amino acid residue (numbering according to Kabat).
9. The humanized anti-BRDU antibody according to any one of embodiments 1 to 8, wherein the antibody has at position 58 of the heavy chain a phenylalanine amino acid residue (numbering according to Kabat).
10. The humanized anti-BRDU antibody according to any one of embodiments 1 to 9, wherein the antibody has at position 108 of the heavy chain a threonine amino acid residue (numbering according to Kabat).
11. The humanized anti-BRDU antibody according to any one of embodiments 1 to 10, wherein the antibody has at position 49 of the light chain a lysine amino acid residue (numbering according to Kabat).

12. The humanized anti-BRDU antibody according to any one of embodiments 1 to 11, wherein the antibody has at position 98 of the light chain a leucine amino acid residue (numbering according to Kabat).
13. The humanized anti-BRDU antibody according to any one of embodiments 1 to 12, wherein the antibody comprises one or more of the following
P at position 30 of the heavy chain variable domain, and/or
F at position 58 of the heavy chain variable domain, and/or
T at position 108 of the heavy chain variable domain, and/or
K at position 49 of the light chain variable domain, and/or
L at position 98 of the light chain variable domain (all positions according to Kabat).
14. The humanized anti-BRDU antibody according to any one of embodiments 1 to 13, wherein the antibody comprises a VH sequence having at least 95% sequence identity to the amino acid sequence of SEQ ID NO: 09 and a VL sequence having at least 95% sequence identity to the amino acid sequence of SEQ ID NO: 10.
15. The humanized anti-BRDU antibody according to any one of embodiments 1 to 13, wherein the antibody comprises a VH amino acid sequence derived from the heavy chain variable domain amino acid sequence of SEQ ID NO: 11 and a VL amino acid sequence derived from the light chain variable domain amino acid sequence of SEQ ID NO: 12.
16. The humanized anti-BRDU antibody according to any one of embodiments 1 to 13, wherein the antibody is a humanized variant of a non-human anti-BRDU antibody comprising the heavy chain variable domain of SEQ ID NO: 11 and the light chain variable domain of SEQ ID NO: 12.
17. The humanized anti-BRDU antibody according to any one of embodiments 1 to 16, wherein the antibody comprises a VH with the amino acid sequence of SEQ ID NO: 09.
18. The humanized anti-BRDU antibody according to any one of embodiments 1 to 17, wherein the antibody comprises a VL with the amino acid sequence of SEQ ID NO: 10.
19. The humanized anti-BRDU antibody according to any one of embodiments 1 to 18, wherein the antibody is a full length IgG1 antibody or a full length IgG4 antibody.
20. The humanized anti-BRDU antibody according to any one of embodiments 1 to 19, wherein the antibody is a monoclonal antibody.
21. The humanized anti-BRDU antibody according to any one of embodiments 1 to 20, wherein the antibody is a bivalent antibody.
22. The humanized anti-BRDU antibody according to any one of embodiments 1 to 21, wherein the antibody is a bispecific antibody.
23. The humanized anti-BRDU antibody according to any one of embodiments 1 to 22, wherein the antibody comprises
a) the heavy chain and the light chain of a first full length antibody that specifically binds to a first antigen, and
b) the modified heavy chain and modified light chain of a second full length antibody that specifically binds to a second antigen, in which the constant domains CL and CH1 are replaced by each other,
whereby either the first antigen or the second antigen is BRDU.
24. The humanized anti-BRDU antibody according to any one of embodiments 1 to 22, wherein the antibody comprises
a) the light chain of a first antibody that specifically binds to a first antigen, and
b) the heavy chain of the first antibody that specifically binds to the first antigen conjugated at its C-terminus to a scFv or a scFab derived from a second antibody that specifically binds to a second antigen,
whereby either the first antigen or the second antigen is BRDU.
25. The humanized anti-BRDU antibody according to any one of the embodiments 1 to 20, wherein the antibody is an antibody fragment that binds BRDU.
26. A complex comprising the humanized anti-BRDU antibody according to any one of embodiments 1 to 25 and a nucleic acid comprising BRDU.
27. A covalent complex comprising the humanized anti-BRDU antibody according to any one of embodiments 3 to 25 and a BRDU conjugated to a cysteine residue.
28. A pharmaceutical formulation comprising the humanized anti-BRDU antibody according to any one of embodiments 1 to 25 or a complex according to any one of embodiments 26 to 27 and a pharmaceutically acceptable carrier.
29. Use of the humanized anti-BRDU antibody according to any one of embodiments 1 to 25 for the delivery of a BRDU containing nucleic acid to a cell.
30. Use of the humanized anti-BRDU antibody according to any one of embodiments 1 to 25 for the delivery of a BRDU containing nucleic acid through the blood-brain-barrier.

V. EXAMPLES

The following are examples of methods and compositions of the invention. It is understood that various other embodiments may be practiced, given the general description provided above.

Example 1

Isolation and Characterization of cDNAs Encoding the VH and VL Domains of a Murine Anti-BRDU Antibody from Mouse Hybridoma The protein and (DNA) sequence information of the VH and VL domains of the murine anti-BRDU antibody was obtained directly from hybridoma clones. The experimental steps performed subsequently were (i) the isolation of RNA from antibody producing hybridoma cells, (ii) conversion of this RNA into cDNA, the transfer into VH and VL harboring PCR fragments, and (iii) integration of these PCR fragments into plasmids vectors for propagation in *E. coli* and determination of their DNA (and deduced protein) sequences.
RNA Preparation from Hybridoma Cells:
The RNeasy Mini Kit (Qiagen) was used to isolate mRNA from hybridoma cells. Approximately $10^6$ cells were lysed in RLT buffer and the lysate was put on a Qiashredder column. The mRNA was concentrated and washed using the RNeasy Mini column.
Generation of DNA Fragments Encoding VH and VH by RACE PCR, Cloning of these DNA Fragments into Plasmids and Determination of their DNA- and Amino Acid Sequences:
cDNA generation and amplification of specific antibody cDNA sequences was done using the SMART Race cDNA Amplification kit (Clontech) according to the protocol of the manufacturer. For the specific amplification the universal primer from the kit and specific primers from the constant region of the antibody light and heavy chain, respectively, were used.

The PCR product was purified by gel electrophoresis and extraction from agarose (QlAquick Gel extraction kit; Qiagen).

PCR products were cloned into pCR4-TOPO vectors (TOPO TA cloning kit for sequencing, Life Technologies). After transformation of E. coli cells, 5-10 colonies were picked, plasmid DNA was isolated according to standard techniques and the cloned inserts were submitted to DNA sequence analysis.

The murine VL sequence of the anti-BRDU antibody is depicted in SEQ ID NO: 12.

The murine VH sequence of the anti-BRDU antibody is depicted in SEQ ID NO: 11.

Example 2

Humanization of the VH and VL Domains of Murine Anti-BRDU Antibody

The murine BRDU-binding antibody was humanized as follows: The generation and characterization of encoding sequences and amino acid sequences that comprise the VH and VL domains of a murine anti-BRDU antibody of the IgG1 class with kappa light chain from mouse hybridoma are described in WO 2011/003557 & WO 2011/003780. Based upon this information, a corresponding humanized anti-BRDU antibody was generated based on the human germline framework IGHV1-18-01 and IGKV3-15-01 combination. The amino acid sequence of the humanized VH is depicted in SEQ ID NO: 09 and the amino acid sequence of the humanized VL is shown in SEQ ID NO: 10.

Example 3

Composition, Expression and Purification of Recombinant Anti-BRDU Antibodies

Murine anti-BRDU antibody variable regions were combined with constant regions of human origin to form mono- or bispecific chimeric antibodies.

The generation of monospecific anti-BRDU antibodies and bispecific anti-BRDU antibodies that specifically bind BRDU as well as a different non-BRDU target (e.g. receptor tyrosine kinases or IGF-1R) required (i) design and definition of amino- and nucleotide sequences for such molecules, (ii) expression of these molecules in transfected cultured mammalian cells, and (iii) purification of these molecules from the supernatants of transfected cells. These steps were performed as previously described in WO 2012/093068.

In general, to generate an antibody of the IgG class that has the binding specificity of the murine anti-BRDU antibody, the VH sequence was fused in frame to the N-terminus of CH1-hinge-CH2-CH3 of a human Fc-region of the subclass IgG1 Similarly, the VL sequence was fused in frame to the N-terminus of human CLkappa constant region.

To generate bispecific antibody derivatives that contain the BRDU-binding specificity as well as specificities to other targets, the anti-BRDU antibody, a scFv or Fab fragment was fused in frame to the C-terminus of the heavy chain of previously described antibodies. In many cases, the applied anti-hapten scFv was further stabilized by introduction of a VH44-VL100 disulfide bond which has been previously described (e.g. Reiter, Y., et al., Nature biotechnology 14 (1996) 1239-1245).

Expression Plasmids:

Expression plasmids comprise expression cassettes for the expression of the heavy and light chains were separately assembled in mammalian cell expression vectors.

Thereby the gene segments encoding the individual elements were joined as outlined above.

General information regarding the nucleotide sequences of human light and heavy chains from which the codon usage can be deduced is given in: Kabat, E. A., et al., Sequences of Proteins of Immunological Interest, 5th ed., Public Health Service, National Institutes of Health, Bethesda, Md. (1991), NIH Publication No 91-3242.

The transcription unit of the κ-light chain is composed of the following elements:
the immediate early enhancer and promoter from the human cytomegalovirus (hCMV),
a synthetic 5'-UT including a Kozak sequence,
a murine immunoglobulin heavy chain signal sequence including the signal sequence intron,
the cloned variable light chain cDNA arranged with a unique BsmI restriction site at the 5' end and a splice donor site and a unique NotI restriction site at the 3' end,
the genomic human κ-gene constant region, including the intron 2 mouse Ig-κ enhancer (Picard, D., and Schaffner, W. Nature 307 (1984) 80-82), and
the human immunoglobulin K-polyadenylation ("poly A") signal sequence.

The transcription unit of the γ1-heavy chain is composed of the following elements:
the immediate early enhancer and promoter from the human cytomegalovirus (hCMV),
a synthetic 5'-UT including a Kozak sequence,
a modified murine immunoglobulin heavy chain signal sequence including the signal sequence intron,
the cloned monospecific variable heavy chain cDNA or the cloned bispecific fusion scFv-variable heavy chain cDNA arranged with a unique BsmI restriction site at the 5' and a splice donor site and a unique NotI restriction site at the 3' end,
the genomic human γ1-heavy gene constant region, including the mouse Ig μ-enhancer (Neuberger, M. S., EMBO J. 2 (1983) 1373-1378), and
the human γ1-immunoglobulin polyadenylation ("polyA") signal sequence.

Beside the κ-light chain or γ1-heavy chain expression cassette these plasmids contain
a hygromycin resistance gene,
an origin of replication, oriP, of Epstein-Barr virus (EBV),
an origin of replication from the vector pUC18 which allows replication of this plasmid in E. coli, and
a β-lactamase gene which confers ampicillin resistance in E. coli.

Recombinant DNA Techniques:

Cloning was performed using standard cloning techniques as described in Sambrook, J., et al., Molecular Cloning: A Laboratory Manual, second edition, Cold Spring Harbor Laboratory Press (1989). All molecular biological reagents were commercially available (if not indicated otherwise) and were used according to the manufacturer's instructions.

DNA that contains coding sequences, mutations or further genetic elements was synthesized by Geneart AG, Regensburg.

DNA sequences were determined by double strand sequencing performed at SequiServe (SequiServe GmbH, Germany).

DNA and Protein Sequence Analysis and Sequence Data Management:

The Vector NTI Advance suite version 9.0 was used for sequence creation, mapping, analysis, annotation, and illustration.

Expression of Anti-BRDU Antibodies and Derivatives:

The anti-BRDU antibodies were expressed by transient transfection of human embryonic kidney 293 (HEK293) cells in suspension. For that, light and heavy chains of the corresponding mono- or bispecific antibodies were constructed in expression vectors carrying prokaryotic and eukaryotic selection markers as outlined above. These plasmids were amplified in E. coli, purified, and subsequently applied for transient transfections. Standard cell culture techniques were used for handling of the cells as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

The cells were cultivated in appropriate expression medium at 37° C./8% $CO_2$. On the day of transfection the cells were seeded in fresh medium at a density of 1-2×10$^6$ viable cells/ml. The DNA-complexes with transfection reagents were prepared in Opti-MEM I medium (Invitrogen, USA) comprising 250 µg of heavy and light chain plasmid DNA in a 1:1 molar ratio for a 250 ml final transfection volume. The monospecific or bispecific antibody containing cell culture supernatants were clarified 7 days after transfection by centrifugation at 14,000 g for 30 minutes and filtration through a sterile filter (0.22 µm). Supernatants were stored at −20° C. until purification.

To determine the concentration of antibodies and derivatives in the cell culture supernatants, affinity HPLC chromatography was applied. For that, the cell culture supernatant containing mono- or bispecific antibody or derivatives thereof that bind to protein-A was applied to an Applied Biosystems Poros A/20 column in a solution comprising 200 mM $KH_2PO_4$, 100 mM sodium citrate, at pH 7.4. Elution from the chromatography material was performed by applying a solution comprising 200 mM NaCl, 100 mM citric acid, at pH 2.5. An UltiMate 3000 HPLC system (Dionex) was used. The eluted protein was quantified by UV absorbance and integration of peak areas. A purified IgG1 antibody served as a standard.

Purification of Anti-BRDU Antibodies:

Seven days after transfection the HEK 293 cell supernatants were harvested. The recombinant antibody contained therein were purified from the supernatant in two steps by affinity chromatography using protein A-Sepharose™ affinity chromatography (GE Healthcare, Sweden) and Superdex200 size exclusion chromatography. Briefly, the antibody containing clarified culture supernatants were applied on a MabSelectSuRe Protein A (5-50 ml) column equilibrated with PBS buffer (10 mM Na2HPO4, 1 mM $KH_2PO_4$, 137 mM NaCl and 2.7 mM KCl, pH 7.4). Unbound proteins were washed out with equilibration buffer. The antibodies (or -derivatives) were eluted with 50 mM citrate buffer, pH 3.2. The protein containing fractions were neutralized with 0.1 ml 2 M Tris buffer, pH 9.0. Then, the eluted protein fractions were pooled, concentrated with an Amicon Ultra centrifugal filter device (MWCO: 30 K, Millipore) and loaded on a Superdex200 HiLoad 26/60 gel filtration column (GE Healthcare, Sweden) equilibrated with 20 mM histidine, 140 mM NaCl, at pH 6.0. The protein concentration of purified antibodies and derivatives was determined by determining the optical density (OD) at 280 nm with the OD at 320 nm as the background correction, using the molar extinction coefficient calculated on the basis of the amino acid sequence according to Pace, et al., Protein Science 4 (1995) 2411-2423. Monomeric antibody fractions were pooled, snap-frozen and stored at −80° C. Part of the samples was provided for subsequent protein analytics and characterization.

The homogeneity of the antibodies was confirmed by SDS-PAGE in the presence and absence of a reducing agent (5 mM 1,4-dithiothreitol) and staining with Coomassie brilliant blue. The NuPAGE® Pre-Cast gel system (Invitrogen, USA) was used according to the manufacturer's instruction (4-20% Tris-Glycine gels).

Under reducing conditions, polypeptide chains related to the IgG showed upon SDS-PAGE at apparent molecular sizes analogous to the calculated molecular weights. Expression levels of all constructs were analyzed by protein-A. Average protein yields were between 6 mg and 35 mg of purified protein per liter of cell-culture supernatant in such non-optimized transient expression experiments.

FIG. 1 shows the results of expression and purification of the humanized antibody that binds BRDU and BRDU derivatives. Reducing and non-reducing SDS PAGE shows composition and homogeneity of humanized antibodies with and without cysteine at position 53 according to Kabat after purification with protein A (MabSelect) and SEC. The molecular weight marker is in the non-labeled lanes. Antibody H-chains (upper band at 50 k) and L-chains (lower band at 25 k) are detectable under reduced conditions as unique bands without presence of visible amounts of additional protein contaminants.

Example 5

BRDU-Binding Bispecific Antibodies Form Complexes with BRDU Containing Payloads

SEC-MALLS analyses were applied to evaluate if and to what degree transferrin receptor (TfR)- and bromodeoxyuridine (BRDU)-binding bispecific antibody (bsAb) are capable of binding to BRDU containing payloads. Therefore, BRDU-DNA was added to TfR-BRDU bsAb at a 2:1 stoichiometric ratio (350 µg; 2.5 mg/ml) and incubated for 30 min. at room temperature for formation of bsAb/payload-complexes. As control reagents we prepared free bsAb (2.5 mg/ml) and free BRDU-DNA (3.2 mg/ml). BRDU-DNA (BRDU-ACC AAG CCT AGA GAG GAG CAA TAC AAC AGT ACA TAT CGC GTG GTA AGC GT; SEQ ID NO: 14) contained one BRDU per DNA molecule at the 5' end of the DNA. Complexes and control reagents were stored at −80° C. until analysis.

The hereby generated complexes and control reagents were subjected to SEC-MALLS analysis to identify and characterize free bsAb, free payload and complexes of both. SEC-MALLS analysis was performed on a Dionex Ultimate 3000 HPLC equipped with Wyatt miniDawnTREOS/QELS and Optilab rEX detectors. Analytes were dissolved at 1 mg/ml in PBS buffer pH 7.4, applied to a Superdex200 10/300GL column at a flow rate of 0.5 ml/min and eluted with PBS buffer pH 7.4 for 60 min.

The results of these analyses (shown in FIG. 1) indicate that BRDU-containing DNA forms defined complexes with the bsAb. These complexes elute from the column at a MW of 244.9 kDa (FIG. 1A) and display a hydrodynamic radius of 6.8 nm (FIG. 1B), allowing the calculation of a stoichiometric ratio of approximately two (1.8) DNA molecules per bsAb molecule. In comparison to that, free bsAb was detected at a MW of 215.4 kDa and its hydrodynamic radius was determined at 6.2 nm. Free BRDU-DNA was detected at a MW of 16.4 kDa.

Thus, it was shown that BRDU-containing DNA is effectively and stoichiometrically bound by TfR-BRDU bsAb, resulting in complexes in a 2:1 molar ratio.

Example 6

Analysis of BRDU-Binding Antibody by Mass Spectrometry

The identity and integrity of the BRDU-binding antibody and its light and heavy chain was confirmed after removal of N-glycans by enzymatic treatment with peptide-N-glycosidase F (Roche Diagnostics GmbH, Mannheim, Germany) by Electrospray ionization (ESI) mass spectrometry with and without prior reduction. Reduction was performed using TCEP. Desalting was performed on self-packed G25-Sephadex-Superfine columns using an isocratic formic acid gradient. ESI mass spectra (+ve) were recorded on a Q-TOF instrument (maXis, Bruker) equipped with a nano ESI source (TriVersa NanoMate, Advion). MS parameter settings were as follows: Transfer: Funnel RF, 400 Vpp; ISCID Energy, 0 eV; Multipole RF, 400 Vpp; Quadrupole: Ion Energy, 3.0 eV; Low Mass, 850 m/z; Source: Dry Gas, 8 L/min; Dry Gas Temperature, 160° C.; Collision Cell: Collision Energy, 8 eV; Collision RF: 3800 Vpp; Ion Cooler: Ion Cooler RF, 800 Vpp; Transfer Time: 140 µs; Pre Puls Storage, 20 µs; scan range m/z 600 to 2000. The MassAnalyzer software (developed in-house) was used for data evaluation. The observed molecular masses of the deglycosylated BRDU-binding antibody and its light and heavy chain were in accordance with the theoretical molecular masses calculated from the amino acid sequences.

The invention claimed is:

1. A humanized anti-BRDU antibody, wherein the antibody comprises a VH with the amino acid sequence of SEQ ID NO: 09 and a VL with the amino acid sequence of SEQ ID NO: 10.

2. A complex comprising the humanized anti-BRDU antibody according to claim 1 and a nucleic acid comprising BRDU.

3. A pharmaceutical formulation comprising the humanized anti-BRDU antibody according to claim 1 and a pharmaceutically acceptable carrier.

* * * * *